(12) United States Patent
Weber

(10) Patent No.: US 6,226,085 B1
(45) Date of Patent: May 1, 2001

(54) METHOD AND APPARATUS FOR SURFACE EFFECT CHARACTERIZATION

(75) Inventor: William L. Weber, Wallkill, NY (US)

(73) Assignee: GretagMacbeth LLC, New Windsor, NY (US)

( * ) Notice: Subject to any disclaimer, the term of this patent is extended or adjusted under 35 U.S.C. 154(b) by 0 days.

(21) Appl. No.: 09/106,200

(22) Filed: Jun. 26, 1998

(51) Int. Cl.$^7$ ..................................................... G01B 11/30
(52) U.S. Cl. ........................... 356/371; 356/446; 356/236
(58) Field of Search .................................. 356/371, 446, 356/236

(56) References Cited

U.S. PATENT DOCUMENTS

| | | |
|---|---|---|
| 5,155,558 | 10/1992 | Tannenbaum et al. . |
| 5,182,618 * | 1/1993 | Heinonen ............................ 356/446 |
| 5,384,641 * | 1/1995 | Imura .................................. 356/446 |
| 5,661,556 | 8/1997 | Schiff et al. . |

FOREIGN PATENT DOCUMENTS

| | | |
|---|---|---|
| 44 23 698 A1 | 4/1996 | (DE) . |
| 0 335 192 | 10/1989 | (EP) . |
| 4-115109 | 4/1992 | (JP) . |

* cited by examiner

Primary Examiner—Richard A. Rosenberger
(74) Attorney, Agent, or Firm—Morgan & Finnegan, L.L.P.

(57) ABSTRACT

A method and system to measure surface characteristics of a specimen. One implementation involves receiving at a receiver optical radiation reflected or scattered from a specimen, the optical radiation including specular components that are spatially encoded by wavelength according to chromatic aberration of the receiver. A measure of surface characteristics is then provided by processing a signal representing the received optical radiation which includes the specular components that are spatially encoded by wavelength according to chromatic aberration. The invention may be implemented with an integrating sphere, in either SCE or SCI mode, and both color and surface effects of a specimen can be measured simultaneously using a single spectrophotometric instrument. In an alternative embodiment, the size of a port opposite a receiver is varied, and for each of a plurality of port sizes, the receiver receives a corresponding optical radiation signal representing optical radiation reflected by the sample. These optical radiation signals are processed to provide a measure of the specimen surface characteristics.

72 Claims, 15 Drawing Sheets

METHOD AND APPARATUS FOR SURFACE EFFECT CHARACTERIZATION

TECHNICAL FIELD

The present invention relates generally to measuring the character or the appearance features of a surface and, more particularly, to a method and apparatus for characterizing and distinguishing color and surface effects using a spectrophotometer implemented with an integrating sphere.

BACKGROUND OF THE INVENTION

The measurement of the visual appearance of objects is of interest and of commercial value. Appearance is composed of several attributes of the object. The "color" generally is produced by the sub-surface diffuse reflection of light where colorants absorb different wavelengths to a varying degree, and is the primary attribute measured with traditional colorimetry instruments. Gloss is a surface appearance attribute, which is usually measured using a different instrument just for that purpose. Other surface characteristics or effects, such as surface undulations and roughness influence the viewed appearance of the specimen, which is not taken into account in normal instrumental color measurements and may in fact interfere with the desired measurement of the color and/or gloss.

Spectrophotometers for colorimetry are often equipped with an integrating sphere for the measurement of a specimen's reflection color. This standardized geometry often includes a means for controlling the specular (mirror like) reflection of the light from the sample. Often the instrument can measure the specimen with the specular component included (SCI) as well as excluded (SCE), which provides some information about the glossiness and smoothness of the specimen surface, but does not discriminate these effects.

U.S. Pat. No. 5,155,558 to Tannenbaum discloses a method and apparatus for analyzing surface appearance which depends on imaging a source aperture mask reflected from the sample, and analyzing the edge spread function of the reflected image of the mask. The image is received by a two dimensional CCD detector array. The edge spread function is interpreted using a Fourier transform to extract the spatial frequencies and associated amplitudes of the sample surface, in much the same way an optical surface or system is analyzed traditionally using the line spread function to reveal the Modulation Transform Function (MTF) of the aberration wavefront. More particularly, many CCD frames are captured while a mechanism scans through focus to optimize the sensitivity of the measurement for each of the various spatial frequencies of interest. A large amount of analysis on each frame is required to provide a line spread function from which surface appearance may be determined. Accordingly, although the method and apparatus of the '558 patent may provide accurate information about the sample surface, it analyzes surface effects only (i.e., it does not by itself also measure color), and it requires precisely controlled mechanical motion, multiple acquisitions, relatively large amounts of data, relatively slow measurement time, and relatively extensive data calculations.

There is a need, therefore, for further improvements in methods and apparatuses for measuring surface effects and/ or surface appearance, and particularly, for measuring and distinguishing both color and appearance attributes of a specimen, preferably with a single measurement of the specimen.

SUMMARY OF THE INVENTION

The present invention, overcomes the above, and other, limitations of prior and background art spectrometers, by providing a method and system for implementing a new measurement modality for measuring surface characteristics or effects, as well as appearance, of a specimen. In accordance with an aspect of the present invention, a method and apparatus for characterizing surface effects of a specimen is provided for receiving at a receiver optical radiation reflected or scattered from a specimen, the optical radiation including specular components that are spatially encoded by wavelength according to chromatic aberration of the receiver (e.g., chromatic aberration of a lens or zone plate). A measure of surface characteristics is then provided by processing a signal representing the received optical radiation which includes the specular components that are spatially encoded by wavelength according to chromatic aberration.

The measure of surface characteristics may be a surface effect index representative of surface roughness and may be determined independently of calculating a function representing the spatial frequency content of the surface. In addition, the measure of surface characteristics may be a function representing the spatial frequency content of the surface, including functions thereof. An appearance measure, such as an indication of gloss/matte, "orange peel", or gross flatness, may be calculated according to the function representing the spatial frequency content of the surface.

In accordance with another aspect of the present invention, an apparatus, such as an integrating sphere, includes a first receiver directed toward a specimen to receive first optical radiation reflected by the specimen. The first receiver has optics which provide chromatic aberration, and the first optical radiation received by the first receiver includes specular components that are spatially encoded by wavelength according to the chromatic aberration. The apparatus also includes a port or trap disposed substantially opposite to the first receiver such that a specular projection of the first optical radiation received by the first receiver overlaps the region contained by the port or trap. A processor processes a signal representing the first optical radiation received by the receiver to generate a measure of surface characteristics of the specimen based on the specular components that are spatially encoded by wavelength according to chromatic aberration.

In accordance with a further aspect of the present invention, both color and surface effects of a specimen can be characterized from a common measurement. Additionally, a plurality of receivers may be used in parallel. In accordance with an aspect of the present invention, a receiver and its corresponding port or trap may be configured to isolate sensitivity to spatial frequency content of the sample surface along predominantly one direction, and multiple such receivers may be used in parallel to concurrently distinguish effects or appearance attributes along different directions of the specimen. In addition, the receivers may be implemented in SCE mode or in SCI mode.

In accordance with yet another aspect of the present invention, a first receiver is directed toward a specimen to receive optical radiation reflected by the specimen, and a port or trap is disposed substantially opposite to the first receiver such that a specular projection of the optical radiation received by the first receiver overlaps the region contained by the port or trap. The size of the port or trap is adjusted to each of a plurality of sizes. For each of the plurality of port or trap sizes, the first receiver receives a corresponding optical radiation signal reflected or scattered from the specimen. A processor provides a measure of surface characteristics for the specimen based on the corresponding optical radiation signals.

BRIEF DESCRIPTION OF THE DRAWINGS

Additional aspects, features, and advantages of the invention will be understood and will become more readily apparent when the invention is considered in the light of the following description made in conjunction with the accompanying drawings, wherein.

DETAILED DESCRIPTION OF THE PREFERRED EMBODIMENT

In accordance with a preferred embodiment of the present invention, a single spectrophotometric instrument is implemented to measure and discriminate the combined color and surface effects of a specimen. Prior to describing such a preferred embodiment in detail, the present invention may be more easily appreciated with reference to FIGS. 1–3, which schematically depict various illustrative measurement configurations for an integrating sphere 1 which includes a cavity having a highly reflective, optically diffuse surface 1$a$ illuminated with a light source 2 (e.g., lamp) via a lamp port 3 to diffusely illuminate specimen (sample) 6 at port 7, in a conventional way.

Figure 1:
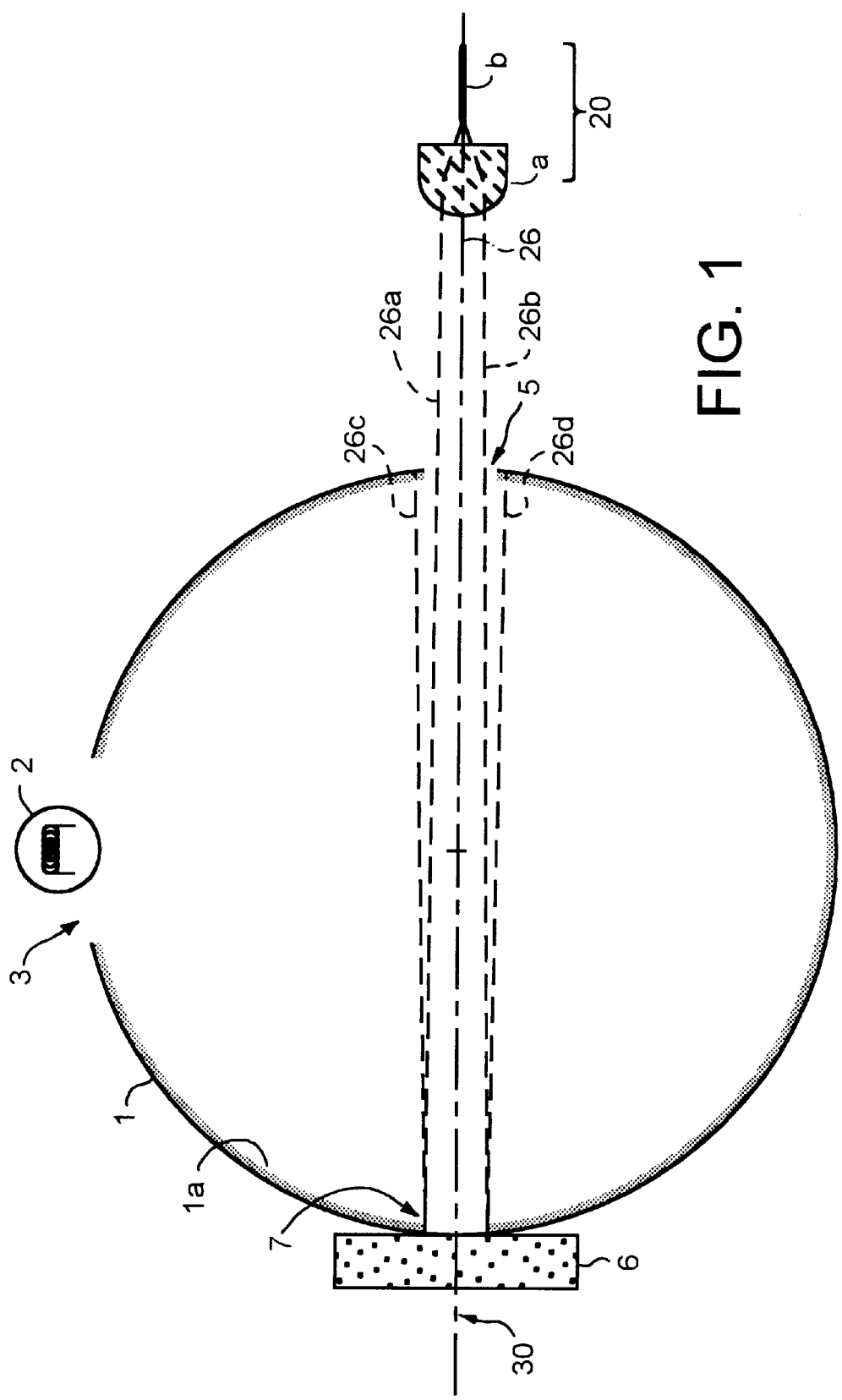
FIG. 1 illustrates an integrating sphere using a classic configuration, generally referred to as Diffuse/0°.
Figure 2:
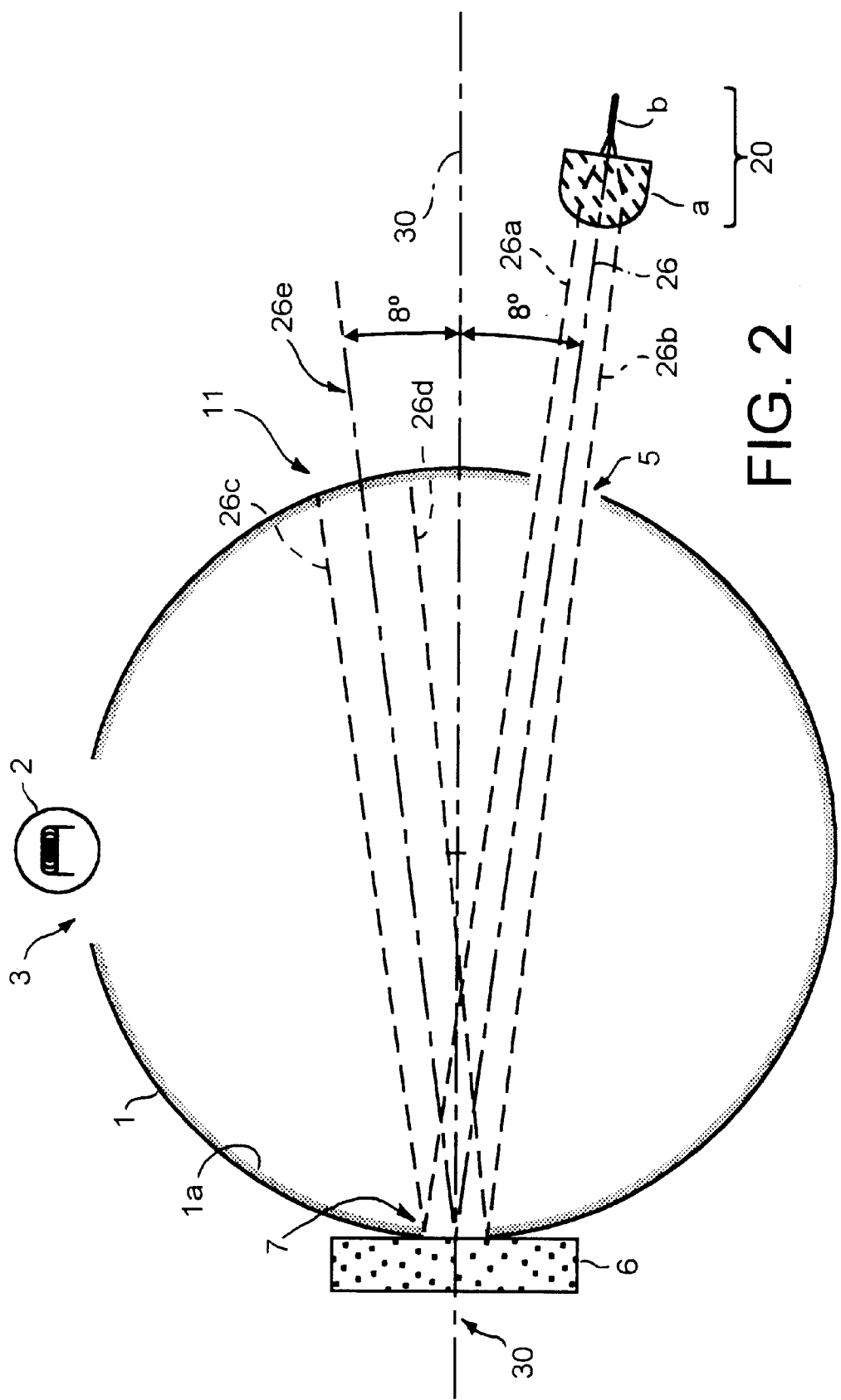
FIG. 2 illustrates an integrating sphere using a classic SCI mode configuration.

More particularly, FIG. 1 illustrates a classic configuration, generally referred to as Diffuse/0°, in which a receiver is positioned to receive optical radiation normal to a diffusely illuminated specimen, and the requisite port in the integrating sphere for the receiver optic automatically excludes all or a portion of the specular contribution. As shown, receiver 20, for example including lens 20$a$ optically coupled to optical fiber 20$b$, is directed toward the sample through receiver viewing port 5 along receiver axis 26 which is coaxial with specimen normal 30, and is coaxial with the central axis of integrating sphere 1 (i.e., the axis which passes through the center of the sphere and is normal to the sample surface). Also shown for reference and clarity of exposition in depicting optical radiation received by receiver 20 (i.e., the viewing beam of receiver 20) are schematic depictions of: viewing beam rays 26$a$ and 26$b$ which represent rays at the outer boundaries of the viewing beam for receiver 20; and specular rays 26$c$ and 26$d$ which are the specular rays corresponding to viewing beam rays 26$a$ and 26$b$, respectively. From these reference lines, it can be seen that in this implementation receiver viewing port 5 excludes all but a small portion of specular components from the view of receiver 20. It can also be seen that, as is well understood, all specular components may be eliminated by modifying the port and/or the receiver optics.

Figure 3:
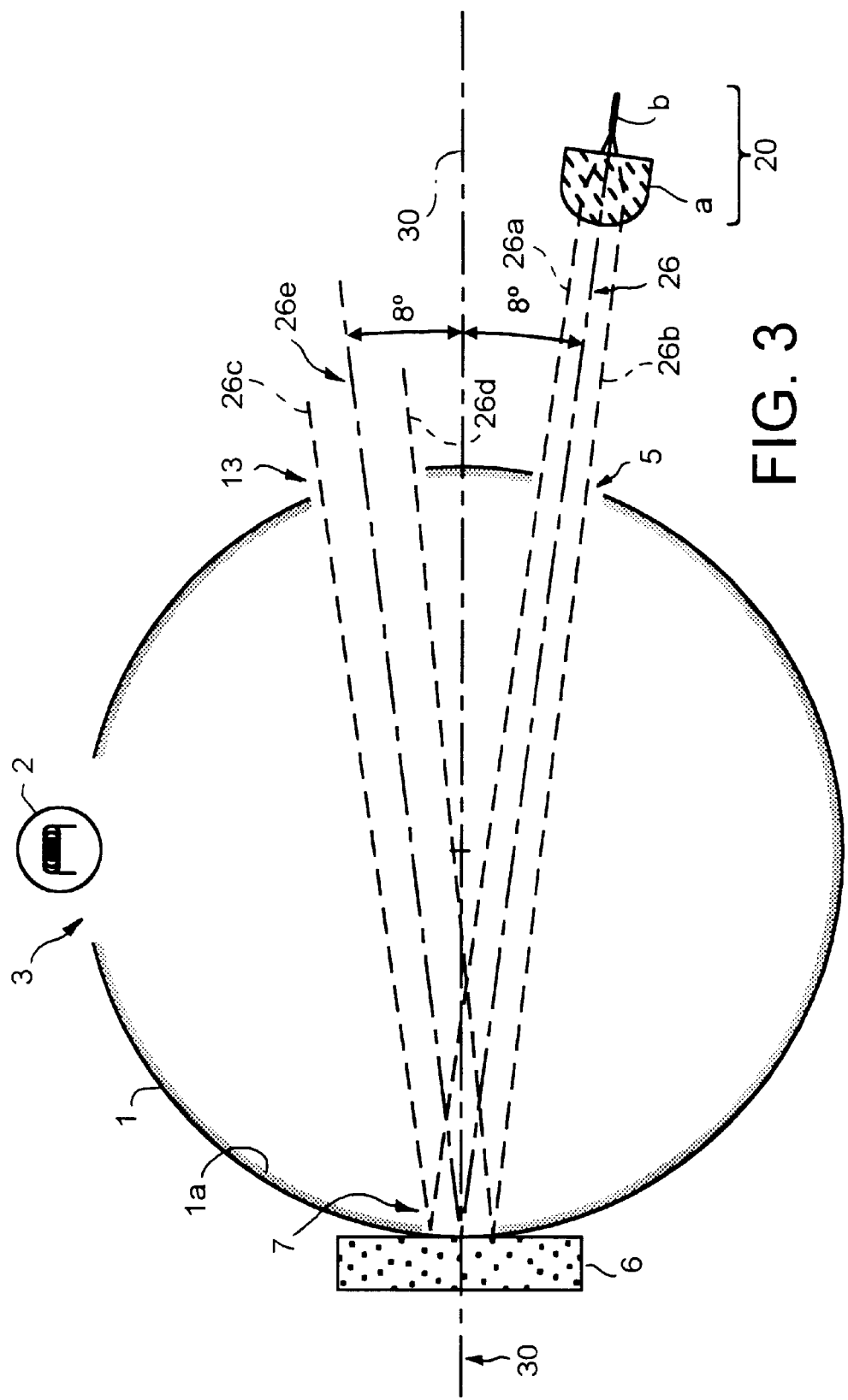
FIG. 3 illustrates an integrating sphere using a classic SCE mode configuration.

Typically, however, the receiver optic axis is generally inclined from the specimen normal (up to 10° per current standards) to allow the specular reflection to be isolated. For example, referring to FIG. 2, with receiver 20 sufficiently inclined from specimen normal 30 (inclination shown, for example, as 8°), specular reflected light can be included (SCI mode) by the presence of the illuminating integrating sphere surface at the region encompassed by the specular projection of the viewing beam of receiver 20, indicated by complementary position 11, which, for the geometric implementation of FIG. 2, corresponds to the region centered about specular receiver axis 26$e$, which is the specular projection (i.e., at the equal and opposite angle from the specimen normal 30) of receiver axis 26. Alternatively, as schematically depicted in FIG. 3, the specular reflected light can be eliminated (SCE mode) by, for example, effectively removing that portion of the integrating sphere surface from where specular components would originate, thus providing what is known as a specular exclusion port 13. As is known in the art, an instrument equipped with a movable portion of the sphere to "plug" the SEP can be used to measure both SCI and SCE separately. Alternatively, an instrument may be equipped with two or more receiver optics, for example including one with a SEP and the other without, to measure SCE and SCI simultaneously, as described in commonly assigned U.S. patent application Ser. No. 09/097,312, entitled "Multi-Channel Integrating Sphere", filed Jun. 12, 1998, which is incorporated by reference herein, and in accordance with the spectrometer disclosed in commonly assigned U.S. patent application Ser. No. 09/041,233, entitled "Concentric Spectrometer", filed Mar. 12, 1998, which is also incorporated by reference herein. For clarity of exposition, embodiments of a multichannel integrating sphere as disclosed in U.S. application Ser. No. 09/097,312, and which may be adapted to implement various embodiments of the present invention, are described hereinbelow following the ensuing description of various embodiments of the present invention.

It is understood that if the specimen has an optically flat and smooth surface ("glossy"), then surface reflection is purely specular and well defined, and thus the SEP need only be slightly larger than the projected receiver beam size for reliable SCE measurements (i.e., negligible reception of specular components). If, however, the specimen surface is not flat and smooth, optical radiation originating from the integrating sphere outside the SEP may be Fresnel reflected by the sample surface to the receiver and will contribute to the measured specimen color (which for SCE should be based on only diffuse reflection). Accordingly, usually the SEP is somewhat larger than the minimum defined by a flat and smooth surface to allow for, some typically minor amount of, such specimen surface variations as well as for small misalignments.

In accordance with the present invention, and as may be appreciated from the foregoing, by acquiring a series of nominally SCE measurements as a function of the SEP size, information about the character of the specimen surface can be extracted from these measurements because the "mapped" angular distribution of the surface reflections is related to the specimen surface profile. Such a method can be implemented, for example, by using a conventional colorimeter/reflectometer having an integrating sphere with an SEP port fitted with, for example, a rotatable aperture wheel of various sized openings which may be individually positioned over the SEP port by rotation of the aperture wheel. More especifically, by way of example, a number of different sized openings may be positioned circumferentially about the aperture wheel (e.g., circular openings angularly displaced about, and having centers equidistant from, the center of the aperture wheel), and the region(s) of the wheel which surrounds each opening and "sees" the sphere interior being diffusely and highly reflective. Alternatively, the rotatable aperture wheel need not have openings to provide for specular exclusion; for example, the openings may be replaced by light absorbant (e.g., "black") material surrounded by the diffusely and highly reflective material. In any such implementation, one position of the aperture wheel may include an opening or space larger than the port such that the port size would be the SEP size.

It may also be understood that more than one such aperture wheel may be used together to provide for additional aperture sizes. For example, a first aperture wheel would include a first monotonic range of aperture sizes, and a second aperture wheel would include a second monotonic range of aperture sizes. The first aperture wheel would be juxtaposed between the SEP port and the second aperture wheel, and preferably would include an aperture or space larger than the SEP port about which it is positioned when the second aperture wheel is used to establish the SEP aperture size. The axes of the different aperture wheels may be mounted coaxially or separately. In any such aperture wheel implementations, the aperture wheel(s) may be rotated by means of a motor (e.g., stepper motor) controlled by a processor used in the spectrophotometer instrument.

In an alternative implementation of a mechanically variable SEP, instead of having a port through the integrating sphere which is variably decreased in size by overlaying aperture masks of different (smaller) sizes, a light trap or baffle (e.g., "black" plug) mechanism may be fed through the integrating sphere wall, and the cross-sectional area of the light trap interior the integrating sphere may be mechanically varied. For example, the light trap may be implemented as an "umbrella-like" mechanism with an elastic-membrane trap which occludes a variable cross-sectional area of the integrating sphere inner surface depending on the extent that it is "opened".

Accordingly, it may be appreciated that, in accordance with the foregoing illustrative implementations of the present invention, specimen surface characteristics may be determined from a "mapped" angular distribution of the surface reflections measured for different SEP sizes. It is understood, however, that these foregoing illustrative implementations, while capable of providing for specimen surface characterization concurrently with a color measurement (i.e., if color measurement is also desired), nevertheless require many measurements and a mechanically variable SEP.

In accordance with a preferred embodiment of the present invention, such a "mapped" angular distribution to characterize the specimen surface profile is obtained without requiring multiple measurements and a mechanically variable SEP, by exploiting chromatic aberrations of a lens or a zone plate, for example, to map the angular distribution according to wavelength.

More specifically, a conventional single element lens usually has chromatic aberrations resulting from the wavelength dependent variation in the index of refraction of the optical material. Normally, a positive lens has a shorter focal length for shorter wavelengths of light due to a higher index of refraction. This effect is often a problem that needs to be reduced by using multiple lens elements of two or more materials, which adds cost and limits the Numerical Aperture or "speed" of the optical system.

Figure 4:
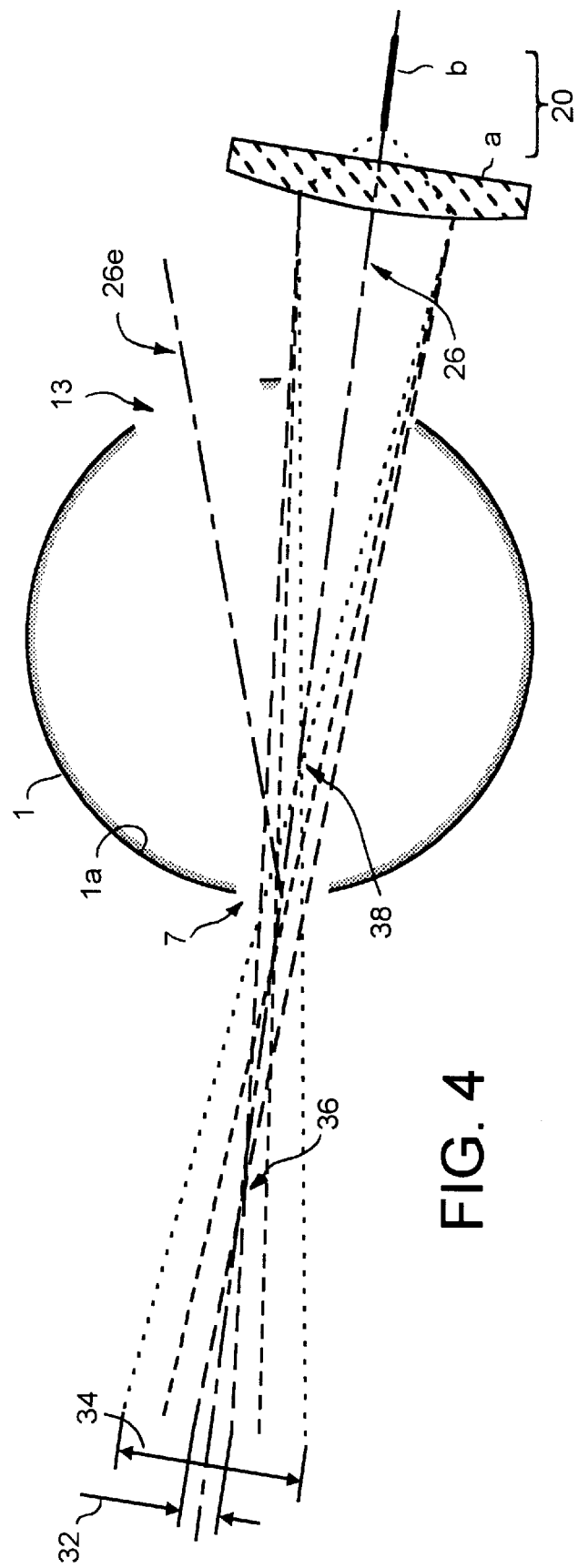
FIG. 4 schematically illustrates an integrating sphere configuration and associated schematic specular rays for implementing an embodiment of the present invention.

The present invention, as preferably embodied, does not attempt to reduce the effect of the receiver lens chromatic aberration, but instead exploits it. The effect of this chromatic aberration is that the projected size of the receiver beam at the SEP location is a predictable function of the wavelength. Referring to FIG. 4, the size of SEP 13 is chosen to match the projected beam size at a given (i.e., predetermined) wavelength for an ideal flat/smooth nominal specimen (specimen not shown). As understood, parameters involved in effecting the SEP size are the lens material (e.g., glass, plastic, etc.), the apertures in the receiver optics, the conjugate positions, and the focal length of the lens(es) (the desired size of the sample area to be measured influences these parameters). These parameters provide a predictable specular plane image size vs. wavelength function which is calculated, for example, using optical ray tracing. In this illustrative embodiment, the short wavelengths have a larger projected beam size at the SEP than do the long wavelengths (note that an alternative implementation may have a larger projected beam size for the long wavelengths compared to the short wavelengths), as schematically represented by long wavelength specular image 32 and short wavelength specular image 34, which correspond to specular rays projected onto SEP 13 an ideally flat/smooth specimen for wavelengths respectively longer and shorter than the given (i.e., predetermined) wavelength. Also identified in FIG. 4 for clarity are long wavelength focus 36 and short wavelength focus 38. Thus, for a flat/smooth specimen surface the longer wavelengths would have a projected beam size smaller than the SEP. Any specimen with surface variations, however, will cause longer wavelengths to begin to "see" (i.e., receive specular components from) the edge of the SEP (i.e., longer wavelength radiation originating from the integrating sphere interior surface outside SEP 13 will be reflected by the sample surface into the viewing beam received by receiver 20). That is, for a given wavelength, contributions of a specular component to the measured signal will be a function of the specimen surface characteristics because the projected size of the viewing beam for a given wavelength is, in part, a function of the sample surface characteristics.

The effect is similar to having a variable size SEP, as above, but here the proportional size variation is wavelength encoded in a single SCE measurement by virtue of the chromatic aberration of the receiver beam. If the specimen is measured SCI also, then much can be determined about the specimen from these two measurements, including: color, gloss/matte, "orange peel", gross flatness, etc. As described, although such an SCI measurement may be taken separately by using a sphere with a movable portion that selectively plugs an SEP port, an instrument equipped with two or more receivers, such as that disclosed in commonly assigned U.S. patent application Ser. No. 09/097,312, (described hereinbelow following further description of the present invention); allows for measuring SCE and SCI simultaneously, which further simplifies the process.

Figure 5:
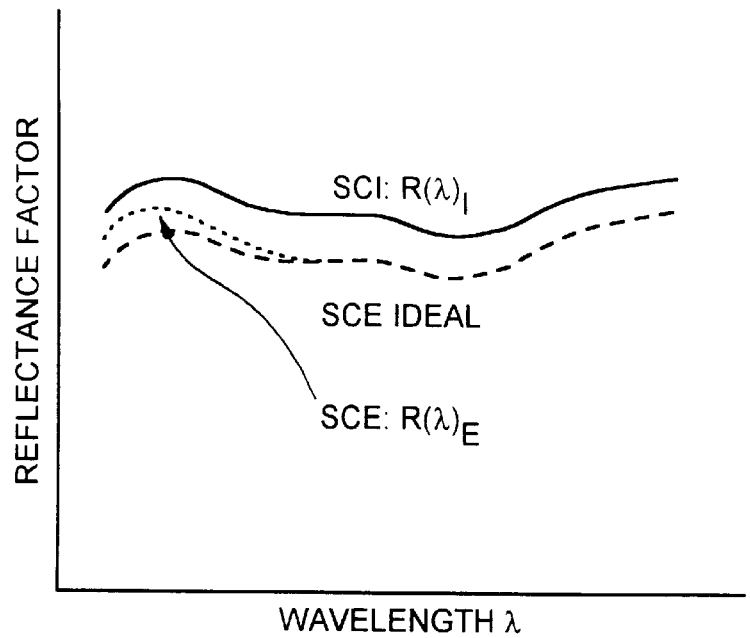
FIG. 5 illustratively depicts spectral reflectances for measurements on a hypothetical specimen having a flat, polished surface, as well as a schematic illustration of the departure of the SCE spectral reflectance, $R(\lambda)_E$ (dotted line), from ideal caused by the chromatic aberration of the receiver optics, in accordance with an embodiment of the present invention.

It is understood that there are many ways of analyzing the acquired data to elucidate surface effects. The specific analysis may depend on various factors, such as the effects, characteristics, or appearance attributes of interest. By way of example, with reference to FIGS. 5–8, an outline of some analysis techniques to evaluate the surface appearance character of a sample from its measured spectral reflectivities are presented as follows, the enumerated ordering provided for clarity of exposition and not for limiting the order of performing any of the enumerated steps or sub-steps of a given enumerated step:

1. The spectral reflectance is first calculated from the acquired data. This process depends on the type of spectral measurement provided by the instrument's spectrometer, calibration techniques, error corrections, etc. This results in spectral reflectances here designated $R(\lambda)_I$, for SCI values, and $R(\lambda)_E$, for SCE values, where $\lambda$ represents the optical wavelength. FIG. 5 illustratively depicts spectral reflectances for measurements on a hypothetical specimen having a flat, polished surface: the ideal d/0 SCE spectral reflectance (dashed line) and the d/0 SCI spectral reflectance, $R(\lambda)_I$, (solid line), are shown. Also shown is a schematic illustration of the departure of the SCE spectral reflectance, $R(\lambda)_E$ (dotted line), from ideal caused by the chromatic aberration of the receiver optics.

Figure 6:
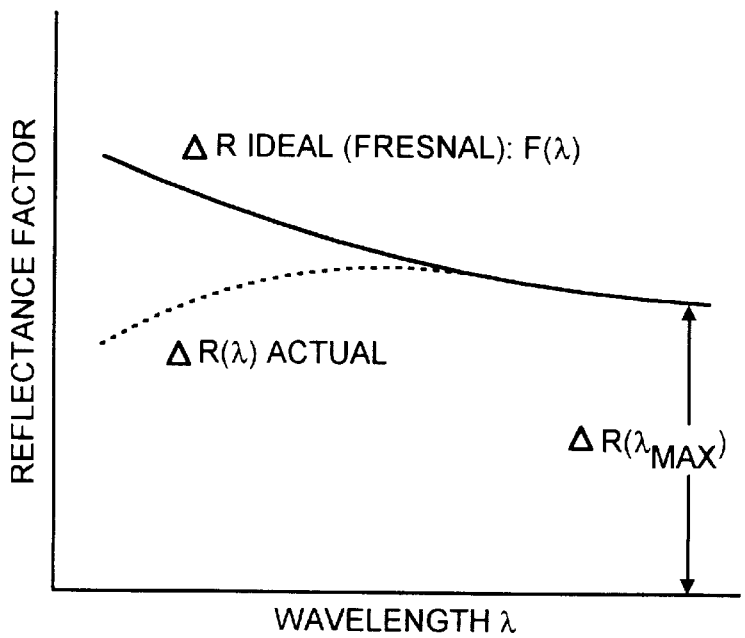
FIG. 6 schematically illustrates the actual and ideal SCI-SCE reflectance differences for the hypothetical sample, in accordance with an embodiment of the present invention.

2. The SCI-SCE difference is then calculated as: $\Delta R(\lambda) = R(\lambda)_I - R(\lambda)_E$ 3. The values of the SCI-SCE difference, $\Delta R(\lambda)$, at the largest wavelength region (the wavelengths in this region denoted by $\lambda_{max}$) of the spectrum are evaluated (for this particular design having the red specular image smaller than the blue) to verify that: a) $\Delta R(\lambda_{max})$ is greater than a predetermined value, and b) data for $\Delta R(\lambda)$ in that region form an adequate fit (predetermined fit criteria based on instrument performance) to the well known Fresnel Reflection Equations for an index of refraction of the sample, n, determined by the average fit in that region. A very diffuse sample surface will fail those criteria and will not be analyzed as below. FIG. 6 schematically illustrates the actual and ideal SCI–SCE reflectance differences for the hypothetical sample, the ideal SCI–SCE reflectance difference representing the Fresnel specular reflectance expected for an ideal aberration-free optical receiver.

4. $\Delta R(\lambda)$ are subtracted from the fitted Fresnel reflectance values, $F(\lambda)$, to yield a reflectance error function, $\epsilon(\lambda) = F(\lambda) - \Delta R(\lambda)$.

Figure 7:
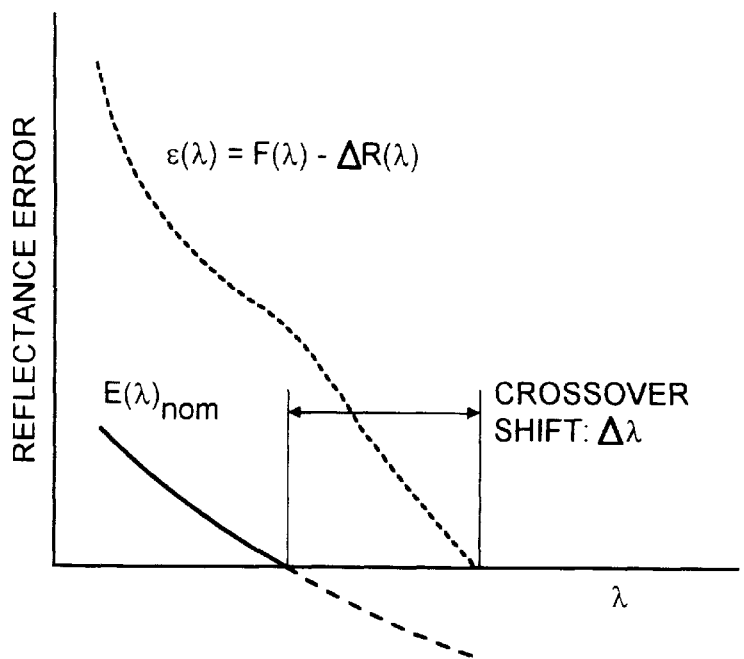
FIG. 7 schematically illustrates the reflectance error function, $\alpha(\lambda)$, for a typical sample with non-ideal specular surface, and the nominal reflectance error function, $\alpha(\lambda)_{nom}$, for a calibration sample, in accordance with an embodiment of the present invention.

5. A perfect specular sample surface will provide a nominal $\epsilon(\lambda)$ function, $\epsilon(\lambda)_{nom}$, that is non-zero for wavelengths shorter than a specific value, the "crossover wavelength". This wavelength value is where the specular image is large enough, and perhaps decentered some, to begin to intersect the edge of the SEP, with shorter wavelengths having an increasingly larger $\epsilon(\lambda)_{nom}$ value. This nominal function can be found before hand by calibration of the instrument using a precision flat surface with known reflectances, such as an optical quality mirror or polished glass. The values for $\epsilon(\lambda)_{nom}$ at wavelengths which are larger than the crossover will measure zero at calibration, but must be extrapolated to negative values based on the data below the crossover wavelength combined with the theoretical knowledge of Fresnel Reflection laws, along with knowledge of the spectral dispersion and focal conjugates of the receiver optics. FIG. 7 schematically illustrates the reflectance error function, $\epsilon(\lambda)$, for a typical sample with non-ideal specular surface, and the nominal reflectance error function, $\epsilon(\lambda)_{nom}$, for a calibration sample.

6. A simple use of the data is to observe the shift in crossover wavelength from $\epsilon(\lambda)_{nom}$ to $\epsilon(\lambda)$. (See FIG. 7). The rougher the sample surface, the larger the shift in crossover wavelength that will result. Accordingly, a useful scale can be generated based on that single parameter (i.e., crossover shift), or on a similar measure of deviation from nominal reflectance error (e.g., differences between integrated areas of $\epsilon(\lambda)$ and $\epsilon(\lambda)_{nom}$), for a simple analysis and characterization of the sample. A more detailed analysis of this data, however, is possible to better characterize the sample surface (e.g., to provide an appearance measure), as follows.

7. The measured (and preferably corrected, as described further below) function $\epsilon(\lambda)$ for the sample has the normalized nominal function $\epsilon(\lambda)_{nom}$ subtracted from it, to yield $E(\lambda)$ which is due to the sample surface "imperfections". More specifically:

$$E(\lambda) = \epsilon(\lambda) - k(\lambda)\epsilon(\lambda)_{nom}$$

where $k(\lambda)$ is used to normalize the calibration values to the sample values for the reflectance of a perfect surface, and is found from the ratios of the calibration standard's known reflectances and $F(\lambda)$. Where $E(\lambda)$ is negative, it is set to zero. The functions $\epsilon(\lambda)$ and $\epsilon(\lambda)_{nom}$ have the beam area integrated into their values. These functions may be differentiated prior to calculating $E(\lambda)$, with any beam non-uniformity accounted for via deconvolution.

Figure 8:
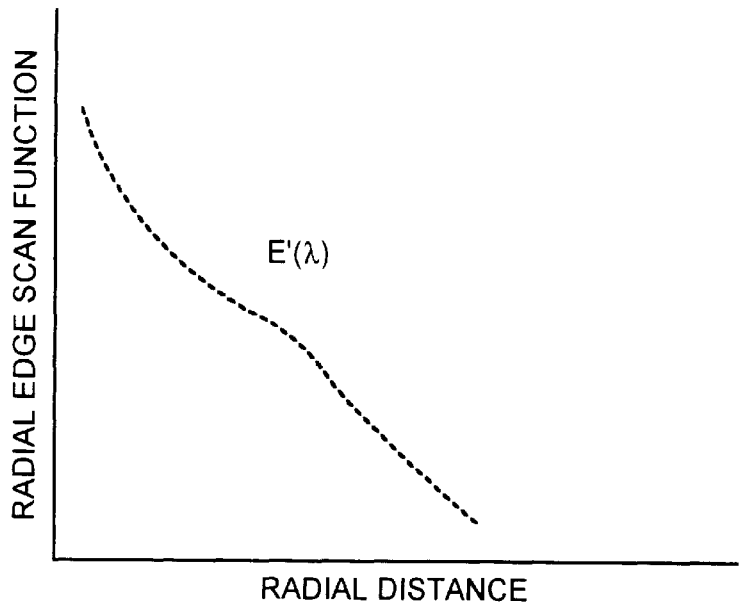
FIG. 8 illustrates an edge scan function for a sample, in accordance with an embodiment of the present invention.

8. The baseline wavelength scale, $\lambda$, of $E(\lambda)$ is next corrected for the nonlinear character of the receiver lens dispersion, which is determined from the lens material(s) and the focal configuration used in the design of the receiver optics. This and/or other correction(s) to $E(\lambda)$ yields the function $E'(\lambda)$, which is the edge scan function of the specular image of the receiver beam. FIG. 8 illustrates the edge scan function for a sample. It may be appreciated that the edge scan function analysis is analogous to the modulation transfer function analysis of an optical imaging system.

9. As is well known in optical testing tradition, and as is applied to appearance measurement by Tannenbaum (supra), $E'(\lambda)$ can be Fourier transformed to provide the spatial frequency distribution content of the sample surface, radially in the case of a round SEP and a round receiver beam.

10. The result can be classified and/or mathematically interpreted on various scales relating to appearance, such as orange peel, haze and the like, in a similar or same way as described and cataloged by Tannenbaum (supra).

From these illustrative data analysis steps, it may be appreciated that selection of the SEP size relative to the projected beam size presents a tradeoff. On the one hand there is a need for having enough data points on the curve from the shortest wavelength to the nominal crossover wavelength to provide a reliable curve shape when calibrating on a polished surface, and thereby allow precise extrapolation of that curve. On the other hand, if the crossover wavelength is too large (e.g., small SEP relative to beam size), then the range of surface roughness measurement becomes more limited since rougher surfaces push the crossover wavelength to longer wavelengths: once the crossover wavelength exceeds the range of the spectrometer, information is lost. By way of example, an SEP size may be chosen relative to the beam size such that the nominal crossover wavelength is roughly between 400 nm and 500 nm for an ideal polished sample surface.

It can be appreciated that there are many alternative methods of analyzing the data, and the above method serves as a general guide to a preferred method, and as such is not intended to be rigorous and detailed. There are many possible alterations or corrections that might be included to account for various instrument configurations and imperfections. For example, the analysis may include corrections for sample translucency and/or uniformity. Additionally, where additional receivers (e.g., having larger area beams) are used, the analysis may also include corrections for receiver beam uniformity and for better determining the sample's Fresnel reflection values, etc. As another example, a configuration may include an additional SCE port which has an SEP size relative to the receiver beam size (and preferably also has the receiver's chromatic aberration eliminated) such that surface effects cause essentially no deviations in measured SCE reflectance over the wavelengths of interest, and the measured SCE reflectance signal for this port may be used instead of, or in addition to, the SCI reflectance measurement to determine deviations from ideal for the SCE port which is subject to variations in measured spectral reflectance due to chromatic aberration.

Additionally, it is understood that there are many possible variations and alternative embodiment possible for implementing the present invention. Various shapes or configurations of the receiver viewing beam and/or SEP may be implemented to better distinguish certain surface characteristics and/or to isolate effects in certain directions. For example, it may be appreciated that the circular SEP configuration with a circular receiver beam as described herein is not necessarily the most advantageous configuration for sensitivity of surface character measurement because the central area of the beam cross-section provides little surface modulated signal, and thus the modulation depth is not optimized. Such a beam geometry, however, is typical for colorimetry and is thus more easily accepted by the industry. As an example of an alternative configuration which would increase the modulation depth, the center of the receiver's viewing beam may be "cored out" to form a hollow cylinder having an annular cross-section and the SEP may be formed as an annular opening (or trap), and thus the surface character effect on the modulation of the signal will have greater depth, or contrast. This latter configuration of a receiver and associated SEP is particularly well suited for implementation as a coaxial receiver, in accordance with the description of coaxial receivers in commonly assigned U.S. patent application Ser. No. 09/097,312 (as described hereinbelow following further description of the present invention). As an example, the annular/cored-out receiver may surround a coaxially disposed SCI receiver which receives specular components from the circular region interior the annular SEP port or trap.

In a similar variation, the SEP may be formed as an elongated rectangle with an appropriately matched receiver beam shape. Such an arrangement may be configured for sensitivity to the spatial frequency content of the sample surface along one direction only (e.g., by selecting the beam size relative to the SEP size in each direction such that only one direction is responsive to wavelength-encoded projected beam size variations due to surface effects), which allows discriminating surface texture variations as a function of the rotational orientation of the sample. A series of such rectangular "slats" may be used with a "striped" beam cross section to increase the amount of light flux available and to provide a beam cross section with a more equal aspect ratio. The spacing of such slats may be chosen to optimize the measurement sensitivity to a particular range of spatial frequencies.

Such configurations using a rectangular SEP and a rectangular beam shape are advantageously implemented using multiple receivers. The orientation and/or the spacing of the slats can be different for each receiver to allow characterization of multiple surface components with one measurement actuation. For example, two such configured receivers may have the same orientation of the rectangle length relative to a normal to the sample but may be azimuthally displaced by about 90° in order to concurrently measure spatial frequency content in orthogonal directions of the sample. Alternatively, the spatial frequency content in orthogonal directions of the sample may be concurrently measured by two such configured receivers which have orthogonally orientated relationships of the rectangle length relative to a normal to the sample and have a common viewing plane (i.e., azimuthally displaced by about 0° or 180°). In such an implementation with 0° azimuthal displacement, the receivers may be disposed coaxially or may be disposed at slightly different viewing angles.

By way of further example of variations within the purview of the present invention, although the hereinabove embodiment is implemented in a spectrophotometer to advantageously discriminate color and surface characteristics in a single measurement, the method of the present invention may be implemented by myriad optical arrangements, not limited to concurrently measuring these appearance attributes. In addition, although the hereinabove described embodiment has been described for a conventional spectrophotometer with an integrating sphere having a diffuse reflectivity measurement configuration (i.e., in which the specimen is illuminated diffusely by virtue of the sphere, and one or more receiver lenses are used to collect the light reflecting from a defined area of the specimen), the "reverse" geometry method could also be used to implement the present invention. That is, the specimen may be illuminated by a defined beam of projected light, with the integrating sphere used to collect the reflected light and to direct the light to an analyzing detector. As yet a further example of variations within the purview of the present invention, although the above preferred embodiment using chromatic aberration is implemented with an SCE receiver structure, the present invention may also be implemented with an SCI mode receiver having chromatic aberration. For example, the SCI receiver may have a circular beam cross-section, and an annular SEP port having an interior highly and diffusely reflective center area (i.e., within the inner boundary of the annulus) would be located opposite the SCI receiver such that the periphery of the projected specular beam for the SCI receiver would overlap the inner boundary of the annulus for wavelengths shorter (or longer, depending on the design) than a given (i.e., predetermined) wavelength for an ideal flat/smooth nominal specimen.

Moreover, although the present invention, and variations thereof, have been hereinabove described predominantly in connection with a preferred embodiment which exploits chromatic aberration, many of the aspects, features, and variations are also applicable to an embodiment of the present invention, briefly described hereinabove, which uses a variable sized SEP port. For example, the port shape and/or receiver beam shape may be appropriately designed to isolate or enhance sensitivity to spatial frequency content along a given direction. For instance, the port may vary in size in one direction only, or the beam shape and/or port shape may be elongated such that isotropic changes in port dimension nevertheless affects predominantly one direction of the received beam. In addition, multiple variable ports may be implemented, and may be oriented to be sensitive to spatial frequency content along different directions of the sample.

As may be appreciated from the above embodiments, and as may be further understood by practicing the present invention, many advantages and attendant advantages are provided by the present invention. For instance, the present invention provides a method for measuring surface effects of a sample such that the method is well suited for implementation with a spectrophotometer used in colorimetry. Additionally, the method permits measurement of and distinction between color and surface appearance with a single measurement using a single instrument (e.g., spectrophotometer). Moreover, such characterization of color and surface effects requires acquiring a relatively small amount of data, and performing a relatively small amount of calculations, thus providing for rapid measurement and characterization. In addition, the present invention may be implemented with a small size (compact) and low weight (e.g., portable) instrument, without requiring moving parts, thus resulting in reduced instrument cost.

Multi-Channel Integrating Sphere

As described, various implementations of the present invention may advantageously employ two or more receivers, which may be implemented in accordance with the invention disclosed by the present applicant in U.S. application Ser. No. 09/097,312. That invention provides an integrating sphere which features the capability of multiple measurement modes (e.g., multiple SCE, SCE and SCI, multiple SCI), multiple areas-of-view for a given measurement mode, multiple viewing angles per measurement mode, and combinations thereof, as will be more fully appreciated hereinbelow. It is noted that the term integrating sphere is not intended to limit the interior cavity to a spherical shape, but is used, as understood by one of ordinary skill in the art, to refer to a class of instruments used for measuring light reflectance of a test sample; different shapes of the interior cavity may be implemented.

Prior to describing illustrative embodiments of the multi-channel integrating sphere invention, certain terminology is introduced for purposes of consistency and clarity of exposition in describing viewing conditions (e.g., spatial/optical location, orientation, and/or relationship of, between, or among port(s), sample, viewing beam(s), etc.) for an integrating sphere which is used in a diffuse reflectance measurement configuration to diffusely illuminate a test sample located at a sample port, and to receive optical radiation reflected from the test sample into receivers associated with viewing ports of the integrating sphere. Conventional calorimeters are often of reverse geometry, that is, with the illumination beam impinging directly on the sample and the detection path receiving light from the wall of the integrating sphere, which integrates the light reflected by the sample. The terminology used herein applies to the "non-reverse" geometry described hereinabove according to a diffuse reflectance measurement configuration.

As used herein, a port generally refers to a region of the integrating sphere in which the highly reflective, optically diffuse inner surface is absent, and typically includes an aperture formed through the inner wall. A colorimeter integrating sphere includes a sample port and one or more viewing ports, and, as described hereinbelow, may also include a specular exclusion port (SEP) and/or a reference port.

Generally, a viewing port has an associated receiver and is characterized by a viewing beam representing the ray bundle of optical radiation received by the associated receiver directly from optical radiation reflected by the sample. The areal cross section of the viewing beam of a receiver at the associated viewing port may be less than or equal to the overall cross-sectional area of the viewing port itself. Where the port area is greater than the receiver area, the region of the port surrounding the receiver portion typically has low reflectivity.

A ray viewing angle refers to the angle between a ray of the viewing beam and the normal to the sample surface where the ray intersects the sample surface. A viewing beam plane refers to a plane defined by a ray in the viewing beam and the normal to the sample surface at the intersection of the sample surface and the ray. An azimuthal angle between two viewing beams is represented by the angle, in a plane perpendicular to a sample normal, between two viewing planes of the respective viewing beams.

Generally, a viewing beam may include rays which deviate from each other (i.e., are not parallel) within some range (e.g., Commission Internationale De L'Eclairage (CIE) Publication Number 15.2 (Colorimetry), 1986, prescribes that the angle between the viewing beam axis and any ray of the viewing beam should not exceed 5°), thus resulting in a finite range of azimuthal angles of the viewing rays relative to a given plane, as well as a finite range of viewing angles for the viewing beam. Since, however, a viewing beam is typically symmetric about a viewing axis (i.e., the central axial ray of the viewing beam), this viewing axis is typically used for describing the (effective) viewing angle for the viewing beam as well as the (effective) azimuthal angle relative to the viewing beam.

Also as used herein, generally for SCE mode, a second port is sometimes said to be opposite relative to a first port (also referred to the first port having an opposing port) if a mirror image beam of the first port's viewing beam mirrored from the sample surface (i.e., each ray of the ray bundle specularly reflected by the sample surface) is substantially overlapped by (e.g., encompassed by) the second port such that the specular component of the first port is completely or effectively excluded. Stated alternatively, the second port encompasses substantially the entire region from which optical radiation specularly reflected from the sample surface into the viewing beam of the first port would originate if the second port were not there (i.e., if the region were diffusely scattering). Stated yet another way, the second port is located at the portion of the integrating sphere wall corresponding to substantially all specular (regular) components for the first port.

Accordingly, two ports are said to be opposite each other if the first port is opposite the second port (as described) and the second port is also opposite the first port such that the mirror image beam of the second port's viewing beam mirrored from the sample surface is substantially overlapped by the first port. It is noted that because a port's receiver area may be smaller than the port's area, if two ports are opposite each other, it does not necessarily follow that the viewing beams view overlapping sample surface regions or that the viewing beams have equal viewing angles: the mirror image of each viewing beam may project into the extra-receiver region of the opposing port, and the extra-receiver region of the port(s) may be of sufficient area to allow for differences in viewing angles and/or viewed sample surface regions. For instance, adjacent, non-concentric (e.g., non-overlapping) sample surface regions may be viewed by ports which are opposite to each other and have the same viewing angle; or, a common, overlapping surface region may be viewed by ports which are opposite to each other and have slightly different viewing angles.

It may be understood in accordance with this terminology that a second port may be opposite relative to a first port but the first port may not be opposite to the second port: the viewing beam of the second port mirrored from the sample surface may not be substantially overlapped by the first port, whereas the viewing beam of the first port mirrored from the sample surface may be substantially overlapped by the second port. For instance, the first port and the second port (i.e., their viewing planes) may be azimuthally displaced by about 180° but with unequal viewing angles such that the second port encompasses a region of the integrating sphere inner surface from where the regular component for the first port receiver would originate but the viewing angle of the second port is such that the first port is not located at the region from where the specular component for the first port arrives. Alternatively, the first and second ports may be azimuthally displaced by about 180° with equal viewing angles, but viewing non-concentric (e.g., non-overlapping) sample surface regions, such that the second port encompasses a region of the integrating sphere inner surface from where the regular component for the first port receiver would originate but the viewed sample region displacement is such that the first port is not located at the region from where the specular component for the first port arrives. In another illustrative alternative, two ports may have any respective combination of viewing angles (including equal viewing angles), and may be azimuthally displaced by any angle not equal to about 180° with the first port's projected beam substantially overlapped by the second port, the ports thus viewing non-concentric (e.g., non-overlapping) surface regions of the sample.

It also follows from this terminology that a second port is said to be non-opposite to a first port if the first port's viewing beam mirrored from the sample surface (i.e., the projection of the first port's viewing beam) is not substantially overlapped by the second port, the first port viewing beam having a not insubstantial specular component. In accordance with this general terminology for describing oppositely disposed ports, it also follows that two ports are non-oppositely disposed if neither port is opposite relative to the other port. For instance, the ports (i.e., their viewing planes) may be displaced by an azimuthal angle different from 180° and have any combination of viewing angles provided neither port's viewing beam projection is substantially overlapped by the other port. Alternatively, it may be appreciated that two non-oppositely disposed ports (i.e., their viewing planes) may nevertheless be azimuthally displaced by about 180° if, for example, they have sufficiently different viewing angles and/or they view sufficiently non-concentric (e.g., non-overlapping) sample regions, such that the projection of each beam is not substantially overlapped by the other port.

It is understood that the foregoing description of spatial relationships between ports (and their viewing beams) is a general one which depends on the relative orientations of the viewing beams with respect to the sample plane (e.g., their respective viewing angles and viewing regions, and their relative azimuthal displacement), and which does not depend on a specific integrating sphere geometry or on a predetermined relationship of the viewing beams to each other or to the integrating sphere geometry.

Typically, however, and in accordance with a preferred embodiment of the multi-channel integrating sphere invention described hereinbelow, each viewing port has a viewing beam that is directed towards the sample along a viewing axis about which the viewing beam is symmetric and which intersects the sample plane at a common point which is typically also the point of intersection of the sample plane by a normal thereto which is a central axis of the integrating sphere (assuming the integrating sphere has a spherical cavity, this central axis passes through the center of the spherical cavity and the center of the sample port). Such symmetry of the viewing beams with respect to a common axis simplifies certain descriptions of relationships between or among ports. For instance, if two ports have equal viewing angles and are azimuthally displaced by about 180°, then they are opposite each other. It is understood, however, that the multi-channel integrating sphere invention is not limited to ports having such spatial symmetry with respect to a common axis which is symmetric relative to the integrating sphere cavity. It is also understood that the foregoing terminology is simply a chosen convention for clarity of exposition, and that there are other ways of describing the spatial relationships between or among ports and their viewing beams.

Figure 9A:
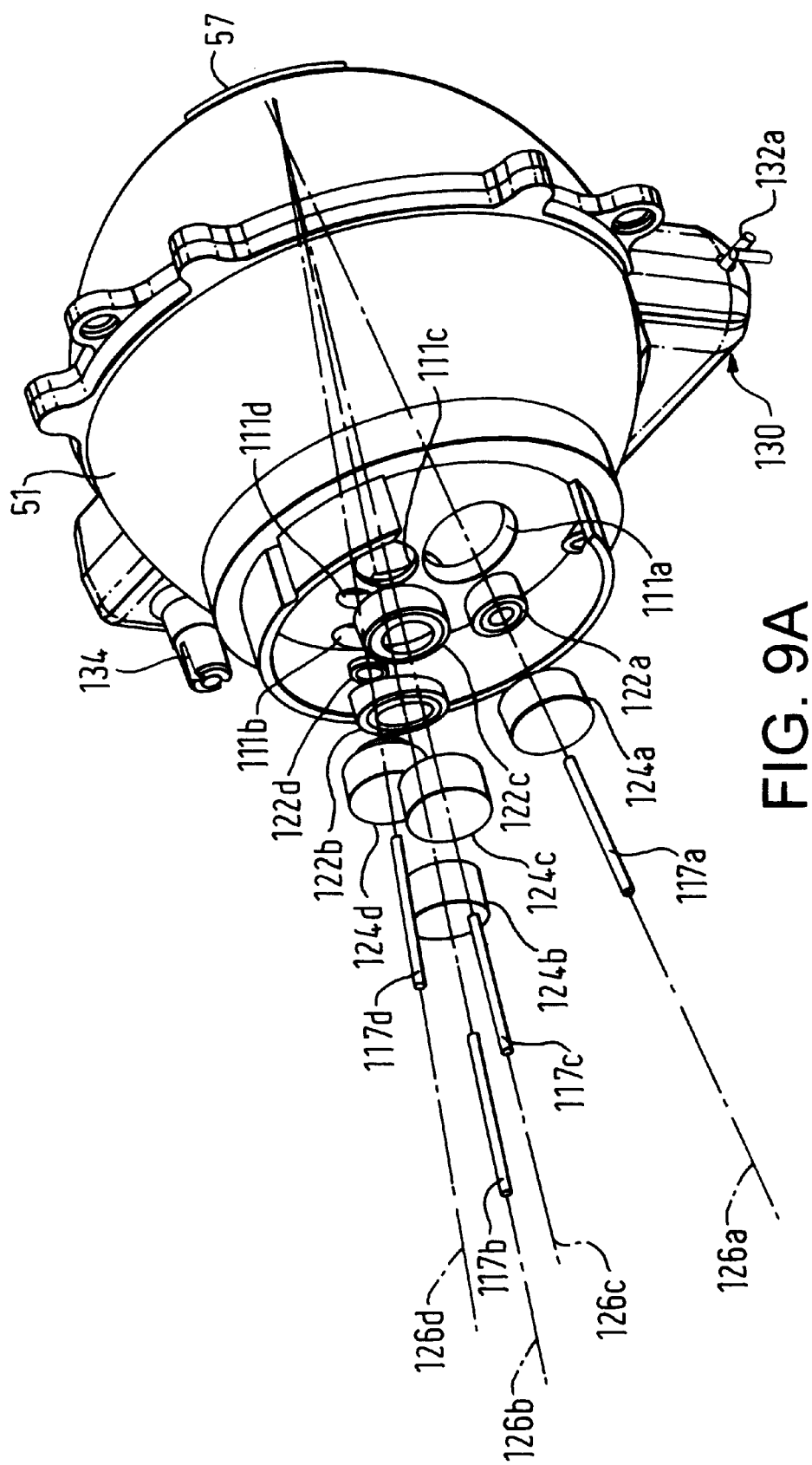
FIG. 9A depicts an isometric view, with certain features of the receivers exposed for clarity, of an integrating sphere that may be used in implementing various embodiments of the present invention.
Figure 9B:
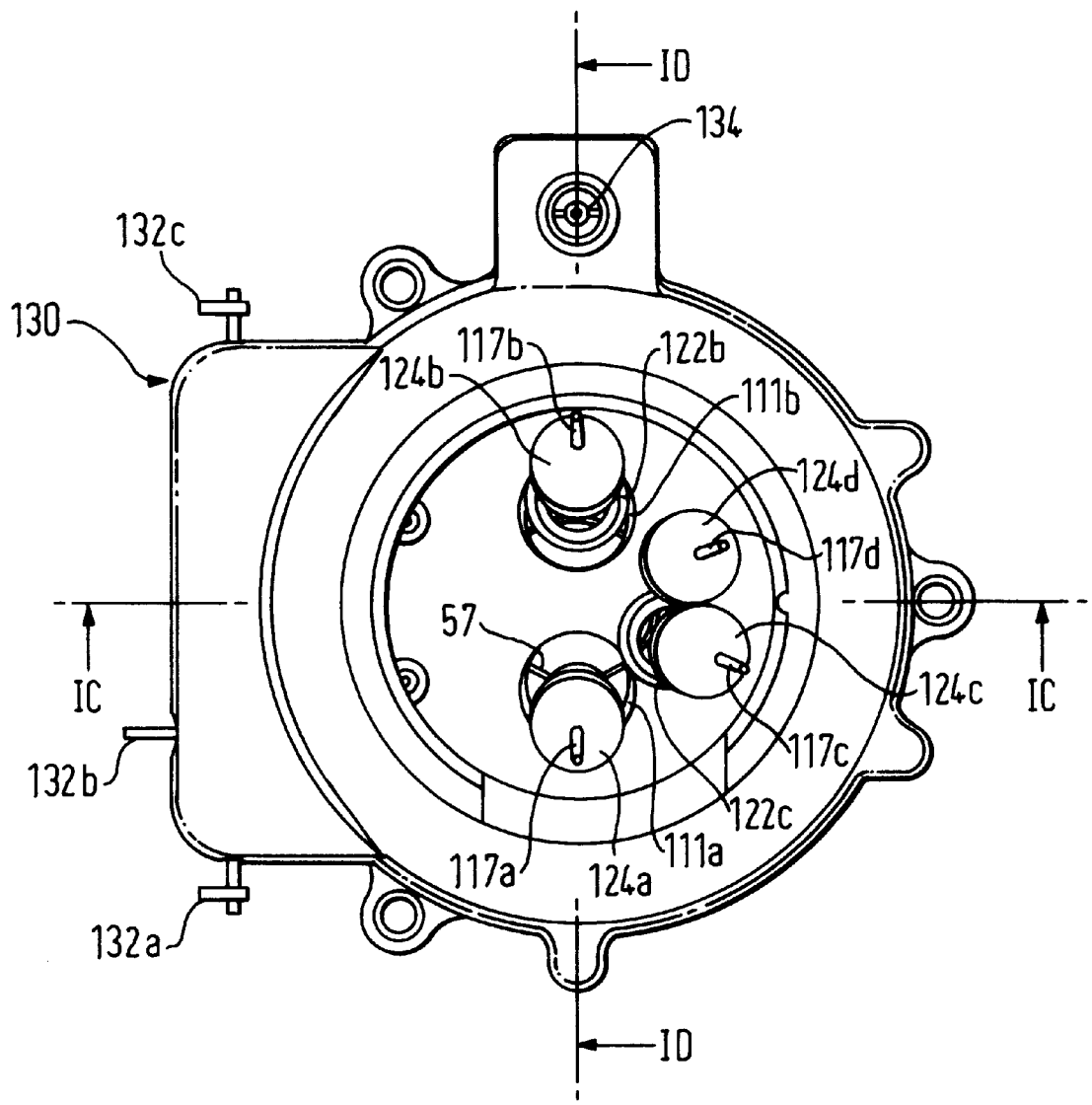
FIG. 9B depicts a plan (top) view, from the receiver side, of the integrating sphere, also with certain features of the receivers spaced away for clarity.
Figure 9C:
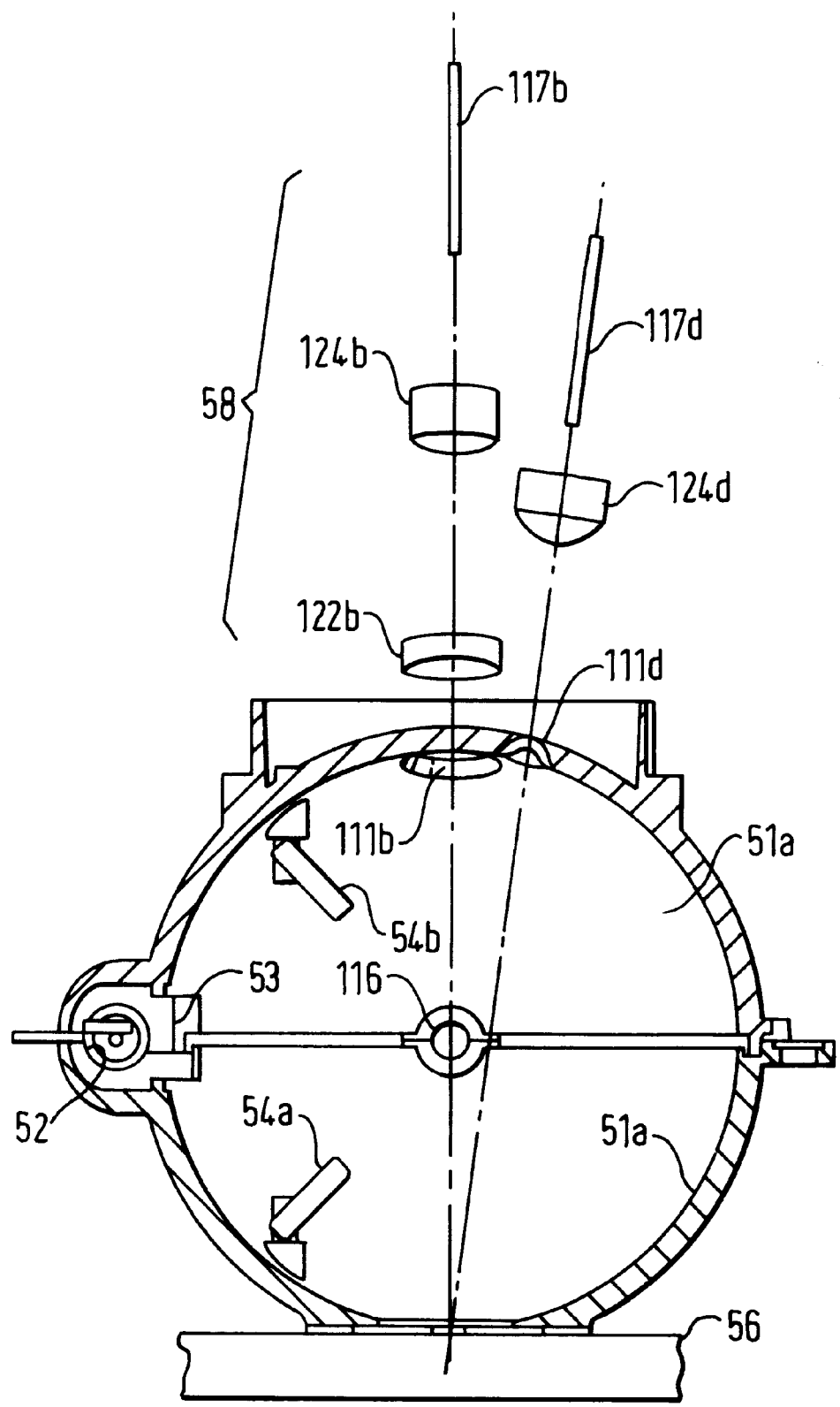
FIG. 9C is a cross-sectional view of the integrating sphere along line IC—IC of FIG. 9B, with certain features of the receivers exposed for clarity.
Figure 9D:
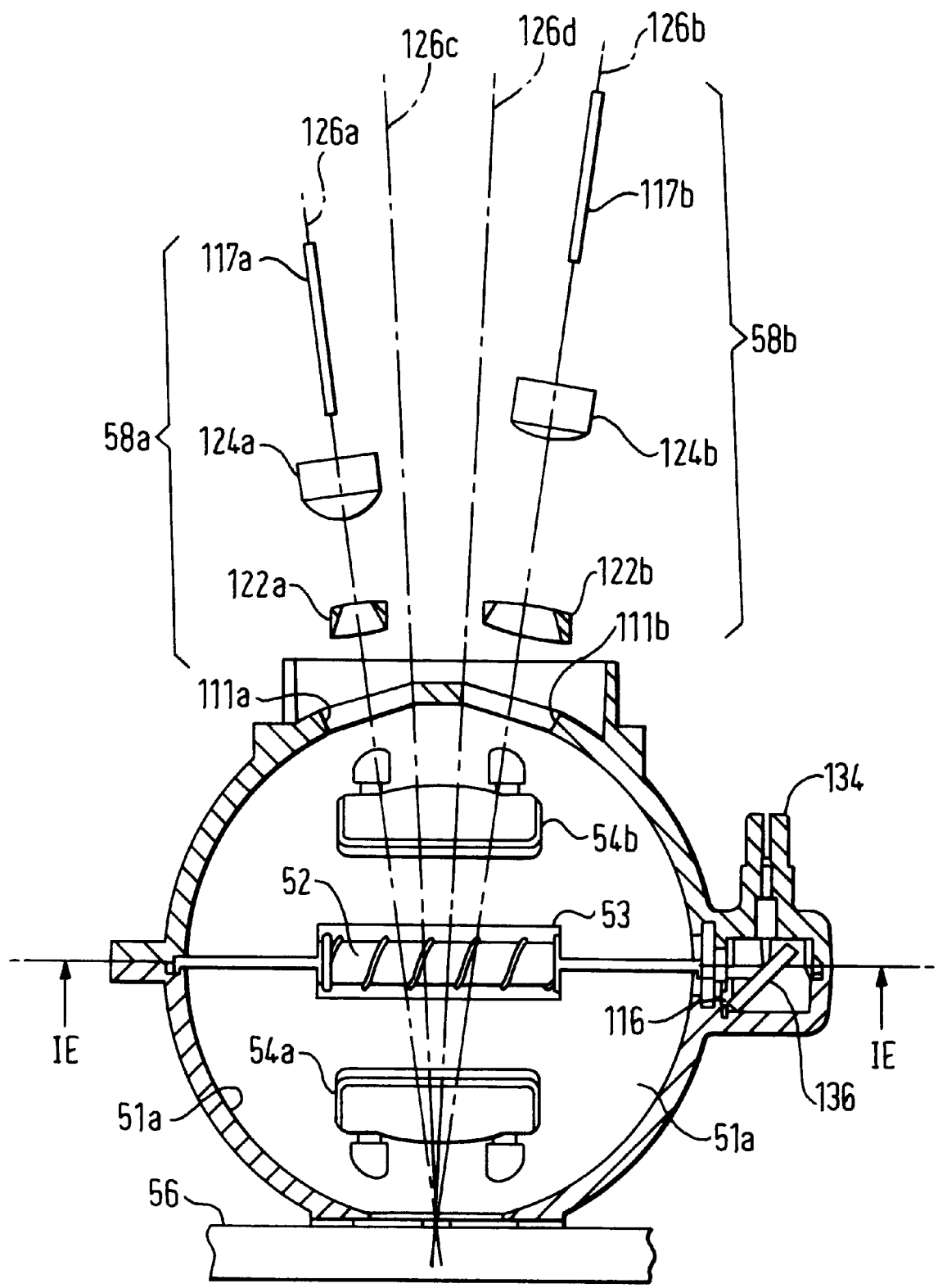
FIG. 9D is a cross-sectional view of the integrating sphere along line ID—ID of FIG. 9B, with certain features of the receivers exposed for clarity.
Figure 9E:
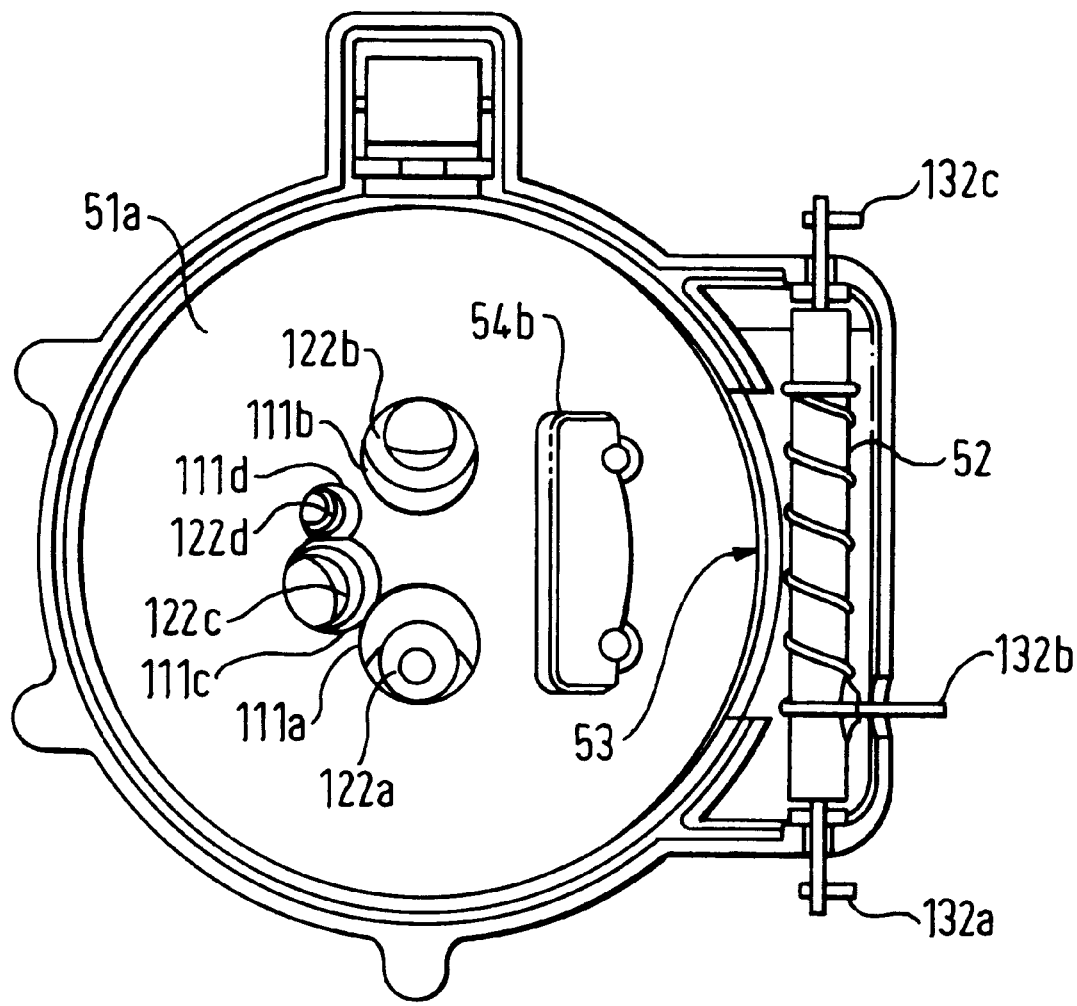
FIG. 9E is a cross-sectional view of the integrating sphere along line IE—IE of FIG. 9D.

Referring now to FIGS. 9A–9E there is shown an integrating sphere 51 according to an embodiment of the multi-channel integrating sphere invention. More specifically: FIG. 9A depicts an isometric view, with certain features of the receivers exposed for clarity, of an integrating sphere according to an embodiment of the multi-channel integrating sphere invention; FIG. 9B depicts a plan (top) view, from the receiver side, of the integrating sphere, also with certain features of the receivers exposed for clarity; FIG. 9C is a cross-sectional view of the integrating sphere along line IC—IC of FIG. 9B; FIG. 9D is a cross-sectional view of the integrating sphere along line ID—ID of FIG. 9B; and FIG. 9E is a cross-sectional view of the integrating sphere along line IE—IE of FIG. 9D.

In more detail, integrating sphere 51 includes two halves to facilitate construction: the two halves may be machined properly to fit one within the other, and appropriately secured with standard fastening mechanisms. Integrating sphere 51 includes a cavity having a highly reflective, optically diffuse surface 51a illuminated with a light source 52 (lamp) which may be coupled to the integrating sphere 51 in a conventional way using an entrance port 53 (aperture in the integrating sphere). Power to the lamp is supplied via lamp leads 132a, 132b, and 132c. By way of example, in an embodiment of the multi-channel integrating sphere invention, the light source 52 may be a pulsed lamp of high intensity, short duration, and with a full "white" spectrum, such as a pulsed Xenon lamp. The effect is to diffusely illuminate sample 56 at port 57, in a conventional way.

In the present embodiment, lamp 52 is external to the integrating sphere 51 cavity, housed in a lamp cavity 130 adjoined to integrating sphere 51. Lamp 52 may alternatively be placed at least partially internal the cavity of integrating sphere 51, and may be placed substantially internal to the integrating sphere cavity to achieve the following advantages: optical flux efficiency, mechanical simplicity, small size, and reduction of port apertures which allows a smaller integrating sphere 51 to be used for a given sample port 57 size while conforming to standards for integrating sphere design. Also, in accordance with conventional practice, the lamp may be external to the sphere and projection optics (e.g., lens, etc.) may be used to relay or project flux from the lamp through the entrance port and to a spot at the far side of the integrating sphere interior.

A baffle 54a with highly reflective, optically diffuse surface is used in a conventional way to block light rays from directly illuminating the sample 56 (shown in FIGS. 9C and 9D, only) from the lamp, or from the entrance port 53 if used. Similarly, baffle 54b prevents light rays originating at entrance port 53 or lamp 52 from directly illuminating portions of the sphere surface from where specular flux for the SCI receivers originates.

As shown, diffusely illuminated sample 56 is viewed by multiple optical receivers 58a–d (i.e., four receivers in the present embodiment), each of which receives a portion of optical radiation reflected from sample 56 and provides it to a sensor or detector used to analyze the spectral content of the received optical radiation. More particularly, shown are multiple viewing ports including specular-component-excluded (SCE) port 111a, SCE port 111b, specular-component-included (SCI) port 111c, and SCI port 111d. Each port has an associated receiver comprising associated receiver optics (shown exposed) according to the present embodiment: SCE port 111a has a receiver 58a including aperture stop 122a, lens 124a, and fiber 117a; SCE port 111b has receiver 58b including aperture stop 122b, lens 124b, and fiber 117b; SCI port 111c has receiver 58c including aperture stop 122c, lens 124c, and fiber 117c; SCI port 111d has a receiver 58d including aperture stop 122d, lens 124d, and fiber 117d. Each receiver 58a–d is directed at sample port 57 along a corresponding one of viewing axes 126a, 126b, 126c, and 126d, which according to the present embodiment, converge to a common point of intersection at the surface of sample 56. It is understood that actual components of the receivers may differ, depending on design criteria, applications, preference, etc.

The optical receivers 58a–d of the present embodiment are located at a same predetermined viewing angle from the sample normal (less than 10° to comply with standards for colorimetry, 8° in the present embodiment) and each has its own associated receiver viewing port 111a–d in the integrating sphere 51. For each viewing mode (i.e., SCE and SCI), the receivers have two subtense angles, corresponding to two sample area sizes. The optical receivers 58a–d and their respective receiver viewing ports 111a–d are displaced azimuthally, thereby advantageously maintaining the same predetermined viewing angle from the sample normal, and the azimuthal displacements are chosen to conveniently fit optical receivers 58a–d (and their associated viewing ports 111a–d), each designed with a combination of chosen parameters. The parameters include, but are not limited to, the measured size of the sample surface, the subtense angles of the receivers, and the inclusion (SCI) or exclusion (SCE) of the specular-reflected light. Additional and non-exclusive parameters (not used in the present embodiment) include multiple viewing angles, and different viewing regions of the sample surface (e.g., non-overlapping, non-concentric).

Integrating sphere 51 includes one SCE mode receiver and one SCI mode receiver for each of two different measured areas-of-view (four receivers total). The two SCE receivers 58a and 58b, having viewing axes 126a and 126b which intersect the sample at a common point, have equal viewing angles and are azimuthally displaced by 180°, and are thereby opposite each other. Further, SCE ports 111a and 111b are sized appropriately to exclude substantially all specular rays for the respectively opposing associated SCE receivers 58b and 58a. SCI receivers 58c and 58d are placed out of the plane defined by the viewing beams of SCE receivers 58a and 58b, and also at the same predetermined viewing angle from the common sample normal located at the intersection of the sample by the viewing axes, such that the specular component is provided by the inclusion of the integrating sphere surface (no ports) at the regions intersected by the respectively projected SCI receiver viewing beams.

As described, in the embodiment of the multi-channel integrating sphere invention illustrated in FIGS. 9A–9E, each SCE port is designed to exclude substantially all specular components for the opposing SCE receiver. Such a shared arrangement of SCE/viewing ports advantageously reduces the total port area required to implement a plurality of SCE ports. It may be appreciated, however, that alternative embodiments of the multi-channel integrating sphere invention may include a separate aperture (port) which does not have an associated receiver and which is appropriately sized and located opposite to an SCE receiver to exclude the specular component origin of the reflected light. Such an aperture is common practice which is known as a specular exclusion port (SEP, also referred to as a light trap), and generally refers to a portion of the integrating sphere's inner surface which does not reflect light, but substantially absorbs it, and which is opposite to an SCE port receiver.

As with frequent conventional practice, integrating sphere 51 preferably includes an added receiver, having associated reference port 116, which provides a measurement of the illumination which is not a direct reflection from sample 56 and preferably not directly incident from lamp 52 or lamp port 53. The viewing beam received via reference port 116 is referred to as a reference beam, and can be used to correct or to control the lamp 52 fluctuations and to compensate for the influence of the sample 56 reflectance on the integrating sphere 51 illumination. In FIGS. 9A–9D, reference port 116 location and its associated receiver characteristics (e.g., viewing axis orientation, subtense angle) are such that only light diffusely reflected from optically diffuse surface 51a of integrating sphere 51 is received. As shown, in order to facilitate common orientation of optical fibers for the present embodiment, the reference beam is conveniently redirected by fold mirror 136 into an optical fiber (not shown) coupled to reference fiber mount 134. It is appreciated that for the multi-channel integrating sphere invention, this reference path is not considered or counted as one of the multiple measurement paths.

The spectral content of the optical radiation collected (received) by each of the multiple receivers is analyzed by any of a variety of conventional means, such as filters or spectroscopic optics and appropriate signal processing (not illustrated). Preferably, the optical radiation collected (received) concurrently (in parallel) by the multiple optical receivers 58a–d is detected (i.e., converted from an optical to an electrical signal) in parallel for each receiver, and further, is also detected in parallel spectrum-wise (i.e., for each receiver, the complete spectrum is detected in parallel). In addition, as more fully described hereinbelow, the optical radiation received by the multiple optical receivers 58a–d is detected substantially simultaneously. Analysis of the detected signals may be performed, for example, in order to condition the detected signal and calculate the sample's color using standard formulae, as described in the referenced CIE publication, supra. For clarity, it is noted that, as used herein, receiving optical radiation is distinguished from detecting optical radiation: the former is used to refer to optical radiation scattered/reflected from the sample surface being coupled into (accepted by) a receiver, whereas the latter is used to refer to received optical radiation being sensed (e.g., converted to an electrical signal) by a detector. Moreover, as used herein, receivers (or ports) are said to concurrently receive optical radiation when optical radiation scattered/reflected from the sample impinges on the receivers in parallel; this concurrent reception does not mean that the concurrently received optical radiation is necessarily also detected concurrently or in parallel, although, as described hereinabove and more fully hereinbelow, such concurrent or parallel detection is generally preferable.

In a preferred embodiment of the multi-channel integrating sphere invention, such parallel detection is implemented by a single spectrometer with a two dimensional detector array and a segmented entrance slit and a single diffraction grating, as described by Palumbo et al. in the commonly assigned U.S. application Ser. No. 09/041,233, entitled "Concentric Spectrometer", filed Mar. 12, 1998, which is herein incorporated by reference. Each segment of the slit is illuminated by a corresponding receiver path, which may be accomplished with fiber optic light guides 117a–117d. Thus, the multiple optical receivers 58a–58d can be conveniently and advantageously detected simultaneously using a single common spectrometer. Additionally, the reference beam may also be advantageously detected and processed in parallel by such a multi-channel spectrometer. It may be appreciated, however, that alternative apparatuses and/or methods may be implemented for concurrently, but not necessarily precisely simultaneously, detecting the optical signals received in parallel by the different SCI/SCE receivers. For instance, signal detection may be time multiplexed among the channels. Alternatively, even where parallel detectors are used, the channels need not be synchronously sampled; e.g., each channel may be independently gated and/or have a different sampling rate and/or sampling time.

Figures 10A, 10B:
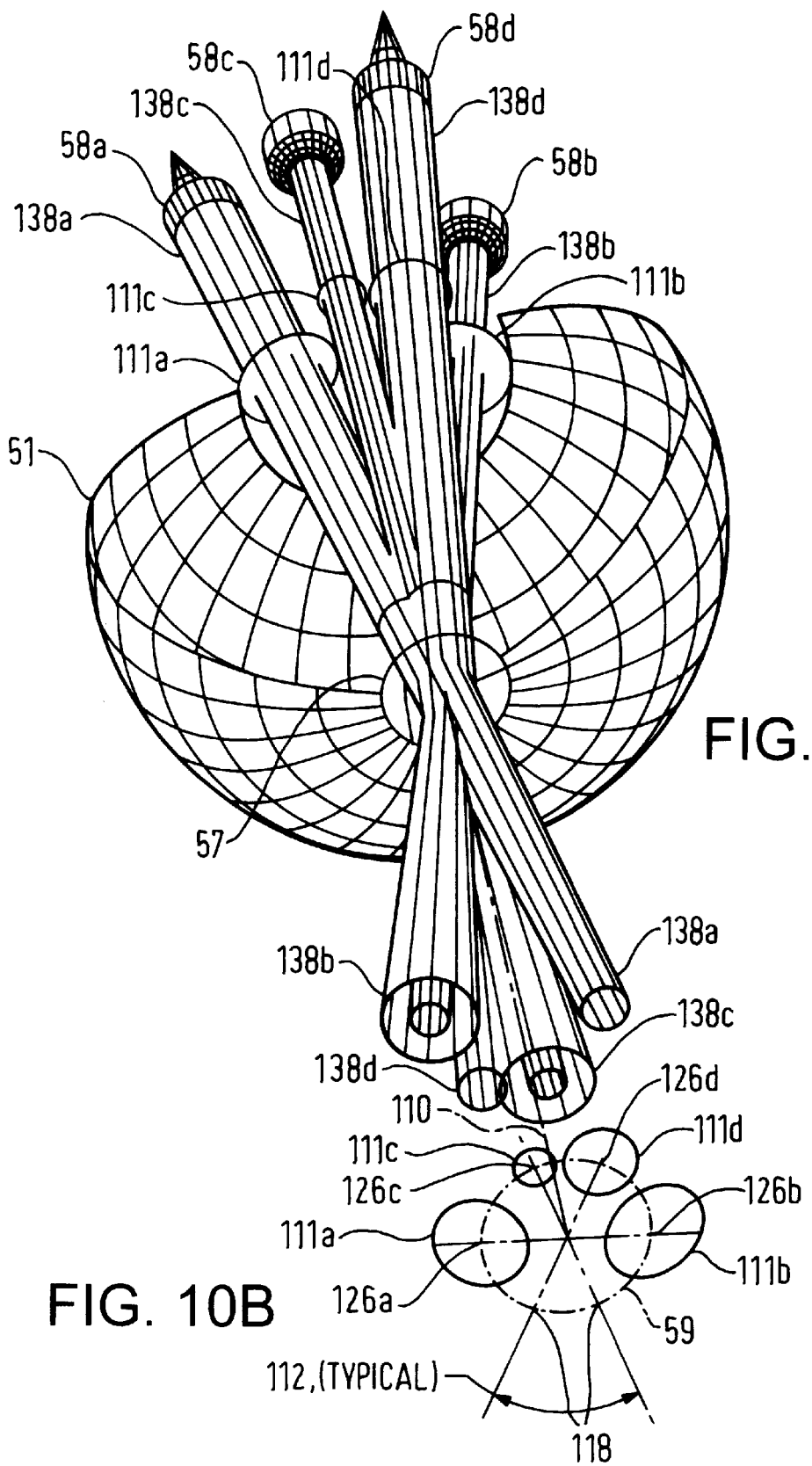
FIG. 10A illustrates a schematic cut-away view of the integrating sphere of FIGS. 9A–9E, with schematic depictions of ray bundles for the receivers and associated ports, so that the relationship among the viewing beams may be visualized.
FIG. 10B shows a projection onto a plane parallel to the sample surface of the receiver viewing ports and viewing axes, as depicted in FIG. 10A, so that the mutual relationships of the ports and viewing axes at the rear (i.e., top portion away from the sample port) of the integrating sphere of FIGS. 9A–9E may be more easily visualized.

Referring now to FIG. 10A, there is illustrated a cut-away view of schematic integrating sphere 51 with schematic depictions of ray bundles 138a–138d for corresponding receivers 58a–58d and associated ports 111a–111d, so that the relationship among the viewing beams of a preferred embodiment may be visualized. Also, referring to FIG. 10B, placed in relation to FIG. 10A, there is shown a projection onto a plane parallel to the sample surface of receiver view ports 111a–111d, viewing axes 126c and 126d (and their projections) of SCI ports 111c and 111d, and viewing axes 126a and 126b of SCE ports 111a and 111b, so that the mutual relationships of the ports and viewing axes at the rear (i.e., top portion away from sample port 7) of the integrating sphere may be more easily visualized. It is noted that in FIGS. 10A and 10B, the schematic depiction of ray bundles preserves the general spatial orientation, but does not preserve the relative sizes, of viewing beams and ports shown in FIGS. 9A–9E. Also identified for reference in FIG. 10B are: an example of an azimuthal displacement angle 112 between SCI ports 111c and 111d (i.e., angle between the viewing planes); common sample normal 110 located at the intersection of the sample by the viewing axes 126a–d; circle 59 defined by the projection of the points of intersection of the viewing axes at the same viewing angle and their corresponding viewing ports; and central points 118 of origination of specular inclusion viewing beams at the rear (i.e., internal surface away from the sample port) of the integrating sphere 51, as would be reflected from the specular reflecting surface of the sample 56. FIGS. 10A and 10B together show the relationship between the ports and the specular components of the beams after reflecting off the sample.

Accordingly, it is appreciated that in accordance with the multi-channel integrating sphere invention, FIGS. 9A–9E illustrate an embodiment of an integrating sphere having multiple viewing ports, with all of the viewing ports have equal viewing angles, the two SCI ports having different sample areas of view, and the two SCE ports also have two different sample areas of view. Advantageously, the SCE ports are disposed opposite each other such that each excludes the specular components for the receiver of the other, thus reducing the overall port area of the integrating sphere.

It is appreciated that various alternative implementations of the multi-channel integrating sphere invention are possible based, as described above, on selection of various parameters including specular component types (i.e., SCI mode and/or SCE mode), number of ports, viewing angles, azimuthal displacements, area-of-view for each port, subtense angles, and viewed sample region for each port. Development of a given design may be dependent not only on certain physical constraints or guidelines, but also on the application or market. For instance, in some applications it is desirable to have a large area-of-view to measure a substantial portion of the sample that provides an average color of a surface that has some variation using a single measurement. It may alternatively or additionally be desirable to have a very small area-of-view to measure a sample that is of small dimension, or a small portion of a multi-colored surface such as a printed pattern or a color bar on a proof sheet, or even to measure the small scale variations of a larger colored surface. Having substantially different, large and small, area-of-views in the same colorimeter may also be generally desireable in order to provide a single integrating sphere having utility for many applications (i.e., multipurpose) or for detecting variations in a sample.

It is understood that the maximum number and size of ports is limited by the sphere diameter which, in order to comply with existing standards, cannot have a total port area (sum of all apertures) that exceeds a certain percentage (3 to 5%, depending on the standards of choice) of the total internal surface area of the sphere. As also is known, the sample port must be slightly larger than the overall region viewed by the receivers to allow for sample translucency (according to existing standards) and to allow for alignment tolerances.

The azimuth angles typically are chosen to adequately separate the viewing ports from one another and from portions of the sphere comprising the origins of specular light for the SCI receivers. These origins of specular light are areas of the sphere surface that are opposite their respective SCI receiver apertures as mirrored from the sample surface, and are of a size that includes preferably all rays that the receiver optics collect by such specular reflection from the sample surface. No ports should intrude those portions of the sphere surface so described. Light traps (SEP ports) or other SCE ports used to remove the specular origin for SCE receivers must be of sufficient size to exclude preferably all rays that the receiver optics would collect by specular reflection from the sample surface.

The size of the receiver ports, specular exclusion ports and specular inclusion origins required are dependent on several parameters of each respective receiver design, including: the sample area-of-view size, the receiver subtense angle, the aperture and focal conjugate positions of a beam forming optic if used (such as a lens), aberration characteristics of the beam forming optic, margin for each beam to ports (respective receiver aperture and specular exclusion) as prescribed by existing standards and/or alignment tolerances, size of the integrating sphere, etc.

As described for the hereinabove embodiment, there is an advantage in opposing SCE ports such that they each effectively act as a specular exclusion port for the receiver of the other SCE port. Such an arrangement reduces the number of ports required for a given number of receivers, and allows more receivers of given parameters to be used in a sphere of the same size.

In the hereinabove embodiment, the receivers's axes are at a same predetermined angle from the sample normal axis, and converge to a common point on the sample surface, the point forming the center of the sample port aperture. For certain applications, however, there may be utility in having receivers at different angles from the sample normal axis and/or not converging to a common point on the sample.

It may be appreciated, therefore, that there are many possible variations for implementing an integrating sphere in accordance with the multi-channel integrating sphere invention. In more detail, for example, although SCE ports 111a and 111b are shown opposite each other, as described, alternatively they may be positioned non-opposite each other (i.e., such that neither port is opposite the receiver of the other port), with each SCE port's receiver having an opposing SEP to exclude the specular component (e.g., (i) SCE ports azimuthally displaced by about 180° but with unequal viewing angles, or (ii) SCE ports azimuthally displaced by an angle not equal to about 180° and having any respective combination of viewing angles, including equal viewing angles).

Alternatively, the illustrative integrating sphere of FIGS. 9A–9E may include two additional SCE ports which are opposite to each other (or a single additional SCE port with opposing trap). For example, relative to opposing SCE ports 111a and 111b, the additional opposing SCE ports (or additional SCE port and opposing trap), may be: (i) azimuthally displaced by about 0° (or, equivalently, by 180°) but at different viewing angles, each one of the additional SCE ports having any general viewing angle and/or area-of-view, or (ii) displaced azimuthally by an angle not equal to about 0° (or equivalently, 180°) and having any viewing angles, including viewing angles equal to each other and to those of SCE ports 111a and 111b.

Additionally, it may be appreciated that there are myriad implementations possible with respect to orientation and arrangement of SCI ports. For instance, SCI ports 111c and 111d alternatively may be displaced by different azimuthal angles (e.g., 90°) and/or disposed at different viewing angles from each other and/or modified to have the same viewing area. Further, one or more additional SCI ports may be added at any appropriate locations on the integrating sphere.

In these arrangements of two or more SCE ports and/or two or more SCI ports, providing azimuthal displacement (e.g., of about 90°) between or among SCE ports and/or between or among SCI ports may be useful for measuring and/or accounting for various appearance or surface characteristics (e.g., striations, texture, etc.) of the sample (e.g., fabric, weaves, embossings, etc.) which may give rise to azimuthally anisotropic reflectance.

Figure 11A:
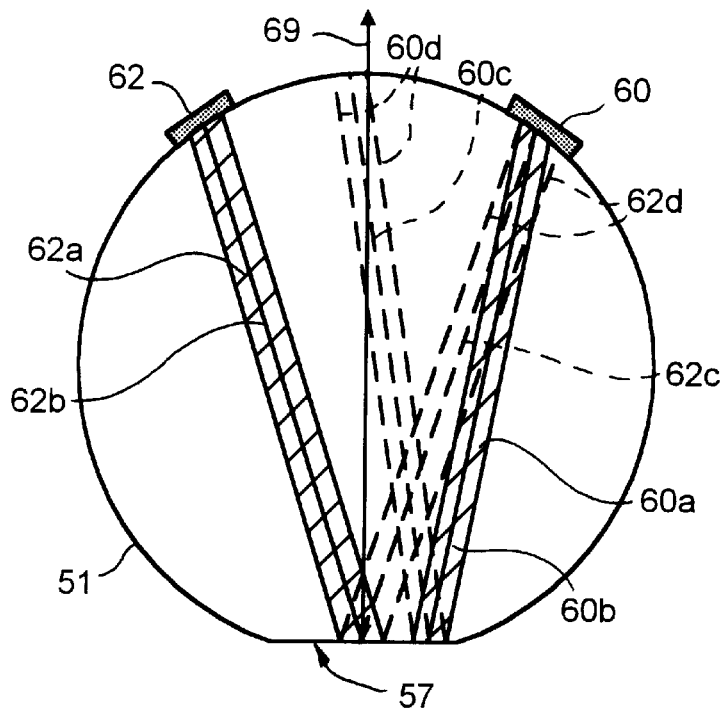
FIG. 11A and FIG. 11B show simplified schematic cross-sectional and top views, respectively, of an integrating sphere having an SCI port opposing the receiver (viewing beam) of an SCE port which does not oppose the receiver (viewing beam) of the SCI port.
Figure 11B:
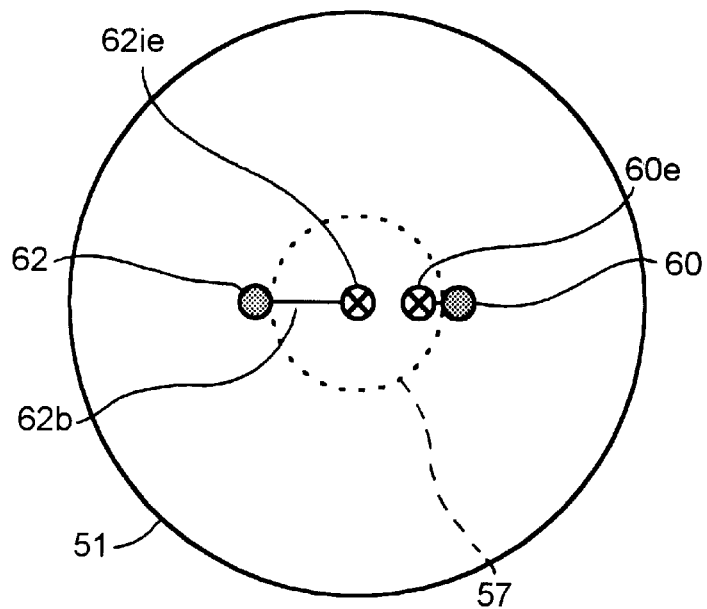

As an additional example of variations within the purview of the multi-channel integrating sphere invention, although the embodiment and illustrative variations described hereinabove includes all viewing beam axes converging to a common point at the sample, alternative embodiments may be implemented wherein viewing axes of different viewing beams do not all converge onto a common point. For instance, viewing axes may intersect the sample at different locations and the corresponding viewing beams may view overlapping sample regions (e.g., a larger viewing area of a first viewing beam encompassing a smaller viewing area of a second viewing beam, or may view two viewing areas each viewing both a common and a separate viewing region) or non-overlapping sample regions. Each sample region may be viewed by more than one viewing beam. For purposes of clarity of exposition, consider the following illustrative port configurations having non-overlapping sample viewing areas:

(1) An SCI port opposing the receiver (viewing beam) of an SCE port which does not oppose the receiver (viewing beam) of the SCI port. As a first example, referring to FIGS. 11A and 11B which show simplified schematic cross-sectional and top views, respectively, of an integrating sphere 51 with sample port 57 and central axis 68, SCI port 60 and SCE port 62 (i.e., their viewing planes) may be azimuthally displaced by about 180° but with unequal viewing angles (i.e., the respective angles between each one of viewing axes 60b and 62b and each corresponding sample normal where the respective viewing axis intersects the sample) such that SCI port 60 encompasses a region of the integrating sphere inner surface from where the regular component for the the viewing beam 62a of the receiver of SCE port 62 would originate but SCE port 62 is not located at the region of the integrating sphere surface from which the specular component for the viewing beam 60a of the receiver of SCI port 60 originates. More specifically, as schematically shown by SCI specular viewing axis 60c (which is the specular reflection of SCI viewing axis 60b) and SCI bounding specular rays 60d (which are the specular reflection of the outer rays of viewing beam 60a), the origin of the specular component for SCI port 60 is located on a diffusely and highly reflective inner surface of integrating sphere 51. Conversely, as schematically depicted by SCE specular viewing axis 62c (which is the specular reflection of SCE viewing axis 62b) and SCE bounding specular rays 62d (which are the specular reflection of the outer rays of viewing beam 62a), SCI port 60 encompasses the region from where the specular component for SCE port 62 would originate. In this example, SCI port 60 and SCE port 62 are shown as viewing non-overlapping areas of view 60e and 62e, respectively, of the sample surface.

Figure 12A:
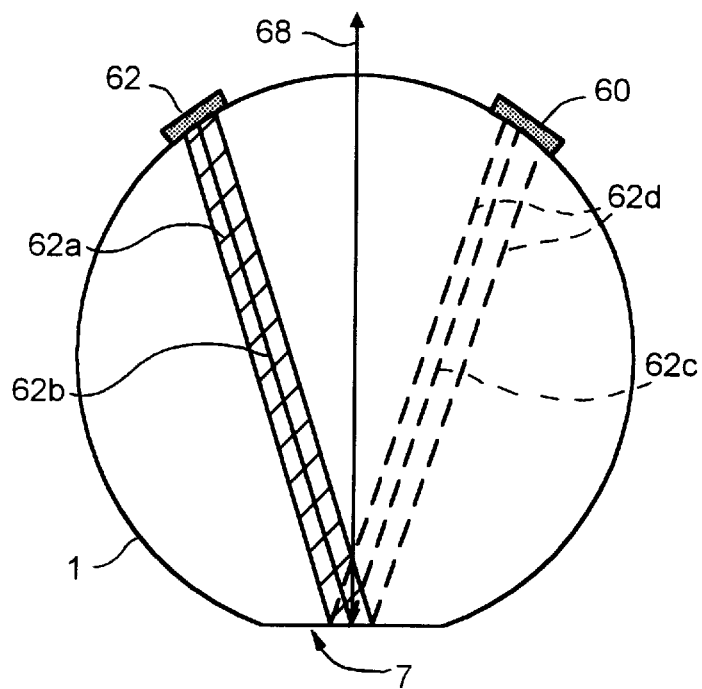
FIG. 12A and FIG. 12B show simplified schematic cross-sectional and top views, respectively, of an integrating sphere having an SCI port opposing the receiver (viewing beam) of an SCE port which does not oppose the receiver (viewing beam) of the SCI port.
Figure 12B:
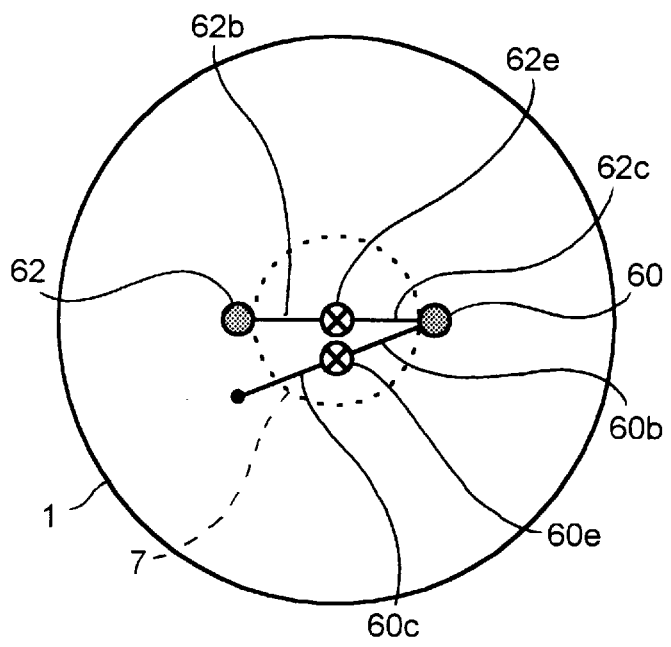

Alternatively, as a second example, referring to FIGS. 12A and 12B SCI port 60 and SCE port 62 (their viewing planes) may be azimuthally displaced by any angle not equal to about 180°, with SCI port 60 and SCE port 62 having any respective combination of viewing angles (within the limits of the integrating sphere geometry), including equal viewing angles, with the projection of the SCE viewing beam reflected from the sample surface impinging on the SCI port. More specifically, as for the previous example, as schematically shown by SCI specular viewing axis 60c (which is the specular reflection of SCI viewing axis 60b), the origin of the specular component for SCI port 60 is located on a diffusely and highly reflective inner surface of integrating sphere 51. Conversely, as schematically depicted by SCE specular viewing axis 62c (which is the specular reflection of SCE viewing axis 62b) and SCE bounding specular rays 62d(which are the specular reflection of the outer rays of viewing beam 62a, SCI port 60 encompasses the region from where the specular component for SCE port 62 would originate. In this example, SCI port 60 and SCE port 62 are also shown as viewing non-overlapping areas of view 60e and 62e, respectively, of the sample surface.

(2) A second SCE port opposing the receiver (viewing beam) of a first SCE port which does not oppose the receiver (viewing beam) of the second SCE port. The second SCE port may be opposed by a SEP or a third SCE port or a SCI port. Various viewing angle and azimuthal angle configurations for the first and second SCE ports are possible, directly analagous to the SCI port and SCE port of the latter example.

(3) A shared viewing port having multiple non-coaxial receivers.

As yet a further example of variations within the purview of the multi-channel integrating sphere invention, the integrating sphere may include coaxial receiver paths (i.e., a single port with a plurality of receivers). More particularly, coaxial receivers can be provided to increase the number of available receivers. An implementation may employ coaxial lenses of different focal lengths and correspondingly different diameters, as would be desired to provide different areas-of-view, and placing them one in front of the other, smaller diameters closer to the sample. The larger lens(es) would peer around the smaller, the latter forming a central obscuration to the larger. The central obscuration can often be tolerated simply as a loss in available sample light for the larger lens(es). The focus of the smaller lens(es) can be transmitted to the analysis means by providing a fold mirror or a fiber optic guide or similar, so as to minimize interference with the larger receiver(s). Of course, curved mirrors may be used instead of the lenses. Another implementation for providing coaxial receivers employs zone plates: a zone plate with a Fresnel pattern is known to have multiple focal lengths, for which a receiver can be used at or near two or more foci, using the transmitting/folding techniques already described. Yet another implementation for providing coaxial receivers is by combining their axes using beam splitter(s) as beam combiners. The coaxial receivers may be implemented as all SCI receivers, all SCE receivers, or a combination of SCI and SCE receivers. The specular component for SCE receiver(s) implemented coaxially with SCI and/or SCE receiver(s) may be blocked by another SCE port (coaxial or individual) or by a SEP. Implementing coaxial SCE ports coaxially with the sample normal provides a plurality of SCE ports without the need for any additional port to block the specular components.

Figure 13:
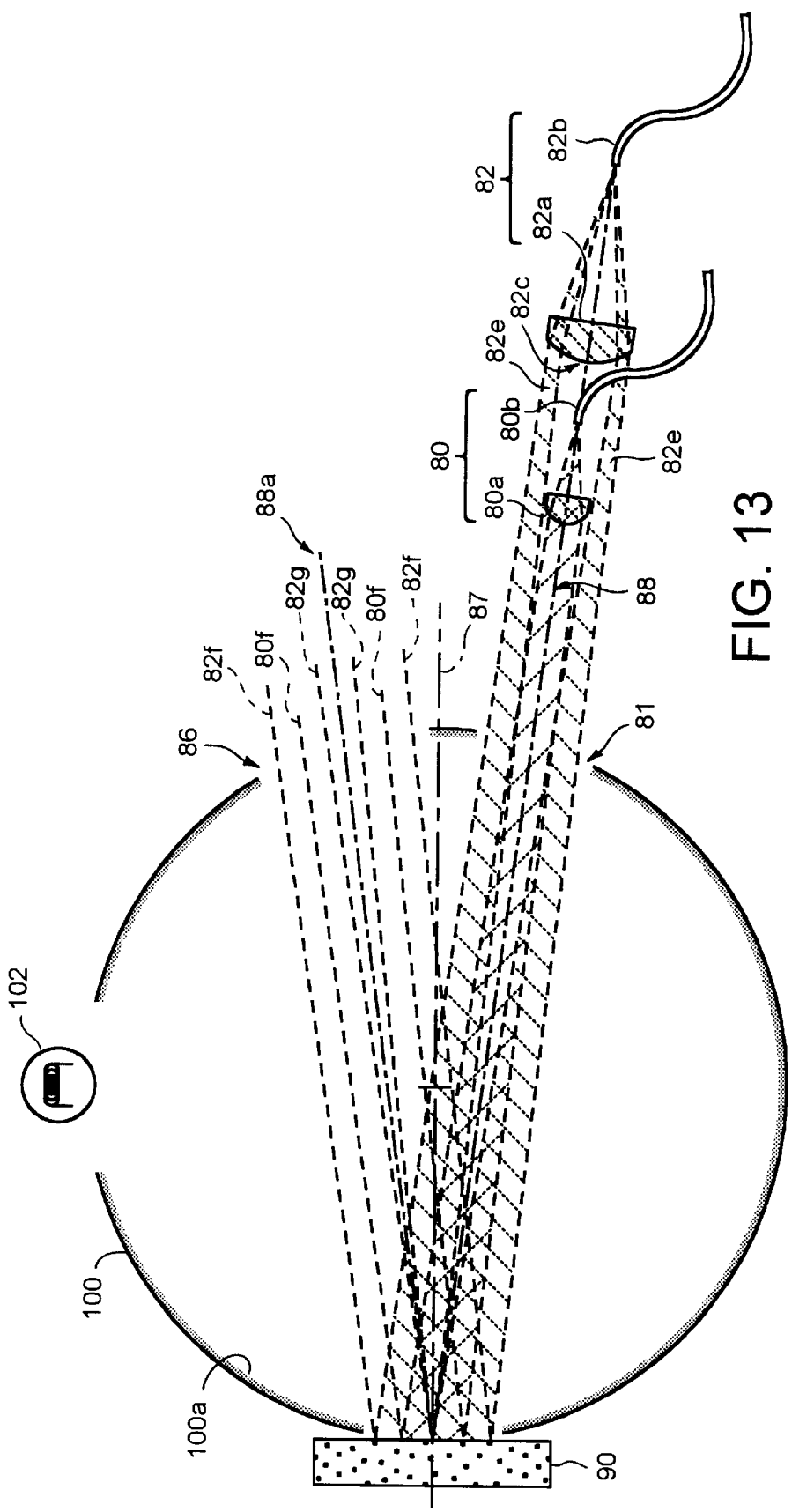
FIG. 13 schematically shows an implementation of an integrating sphere including coaxial receivers.

By way of example, FIG. 13 schematically shows an implementation of a coaxial receiver according to an illustrative embodiment of the multi-channel integrating sphere invention. In this illustrative embodiment, coaxial small area receiver 80 and large area receiver 82 sharing viewing port 81 are both SCE receivers, and are shown as opposed by an SEP 86 which is schematically shown as an absence of a portion of integrating sphere 100 and its inner diffuse, highly reflective surface 100a. Small area SCE receiver 80 and large area SCE receiver 82 have a common receiver axis 88 along which the receivers are directed toward sample 90 which is diffusely illuminated by optical radiation indirectly incident from lamp 102 via integrating sphere 100. Small area receiver 80 includes lens 82aoptically coupled to optical fiber 82b, whereas large area receiver 82 includes lens 82a optically coupled to optical fiber 82b. Lens 82a includes a central obscuration area 82c to prevent receiving optical radiation from the small area receiver, thus ensuring that large area receiver 82 only receives optical radiation directly from sample 90. Also shown for reference and clarity of exposition are schematic depictions of: sample normal 87; specular receiver axis 88a corresponding to the specular reflection of receiver axis 88; small area viewing beam 80e; large area viewing beam 82e; bounding small area specular rays 80f which correspond to the outer boundaries of the specular rays for small area viewing beam 80e; outer large area specular rays 82f which correspond to the specular rays for the outer boundaries of large area viewing beam 82e; and inner large area specular rays 82g which correspond to the specular rays for the inner boundaries of large area viewing beam 82e. From these reference lines, it can be seen that in this implementation small area receiver 80 and large area receiver 82 view concentric areas of sample 90. It is understood that coaxial SCE receivers may alternatively be opposed by another sample viewing port, such as an SCE port (e.g., itself having one or more SCE receivers). It is also understood that, more generally, an integrating sphere in accordance with the multi-channel integrating sphere invention may include one or more ports each having coaxial receiver arrangements, and that additional ports having single receivers may also be included in combination with one or more ports having coaxial receivers.

These foregoing variations with respect to SCE and SCI port arrangements are merely illustrative of the many possible variations according to the multi-channel integrating sphere invention with respect to azimuthal displacement, area-of-view, viewing angle, and location-of-view (i.e., location of area-of-view as may be defined by the sample intersection by the viewing axis) of an integrating sphere having two or more SCI ports, or at least one SCI port and at least one SCE port, or two or more SCE ports. It is understood that, as described above, selection of a particular configuration may depend on various factors, such as intended application(s) (e.g., colorimetry, gloss, texture, etc.) and measurement standards.

As may be appreciated from the foregoing description, and as may be further appreciated by practicing the multi-channel integrating sphere invention, an integrating sphere according to the multi-channel integrating sphere invention includes myriad features, advantages, and attendant advantages. For instance, advantages of receiving a plurality of viewing beams in parallel include: multiple data sets may be provided by a single measurement step, no moving parts or time delay required to change modes (e.g., SCE, SCI, different areas of view for SCE and/or SCI), electrical power is efficiently used (e.g., reduced time needed to power lamp compared to multiple measurements, no parts need be electromechanically moved), component sizes may be small, and overall structure will be durable (e.g., from no moving parts). The presence of both SCI and SCE modes for a given area-of-view can quickly and conveniently provide an estimate of the gloss of the sample surface. The presence of multiple areas-of-view provides capability for quickly measuring or estimating sample uniformity and/or sample translucency. Additionally, various azimuthal angles between SCE and/or SCI provide the ability to extract other appearance parameters (in addition to the color) from the data sets acquired, such as surface flatness or texture. Having a simultaneous reference measurement also provides optimum correction. These features and advantages provide substantial benefits particularly well suited for portable instruments, as well as for convenient non-portable applications.

Although the above description of illustrative embodiments of the invention, various modifications thereof, as well as illustrative embodiments of the multi-channel integrating sphere invention, provides many specificities, these enabling details should not be construed as limiting the scope of the invention, and it will be readily understood by those persons skilled in the art that the present invention is susceptible to many modifications, adaptations, and equivalent implementations without departing from this scope and without diminishing its attendant advantages. It is therefore intended that the present invention is not limited to the disclosed embodiments but should be defined in accordance with the claims which follow.

I claim:

1. A method for characterizing surface effects of a specimen, the method comprising the steps of:
    receiving optical radiation from said specimen, said optical radiation including specular components that are spatially encoded by wavelength according to chromatic aberration; and
    processing a signal representing said optical radiation to provide a measure of surface characteristics based on said specular component that are spatially encoded by wavelength according to chromatic aberration.

2. The method according to claim 1, wherein said specimen is located at a sample port of an integrating sphere, and said receiving is performed by a specular-component excluded receiver disposed through a port of the integrating sphere.

3. The method according to claim 1, further comprising the step of receiving a second optical signal from said specimen, said second optical signal including specular components reflected from said specimen.

4. The method according to claim 3, wherein said optical signal and second optical signal are received concurrently.

5. The method according to claim 1, wherein said processing step includes processing said signal representing optical radiation to provide a color measurement for said sample, thereby providing both color and surface effect characterization for said sample from a common measurement.

6. The method according to claim 1, wherein said measure of surface characteristics is a surface effect index representative of surface roughness and is determined independently of calculating a function representing the spatial frequency content of the surface.

7. The method according to claim 6, wherein said surface effect index is based on a deviation between specular reflectance for the measured specimen relative to an ideally flat and smooth specimen.

8. The method according to claim 6, wherein said surface effect index is based on a shift in crossover frequency of specular error.

9. The method according to claim 1, wherein said measure of surface characteristics is a function representing the spatial frequency content of the surface.

10. The method according to claim 9, wherein said measure of surface characteristics is an appearance measure calculated according to said function representing the spatial frequency content of the surface.

11. The method according to claim 10, wherein said appearance measure is an indication of gloss/matte, "orange peel", or gross flatness.

12. The method according to claim 1, wherein said specular components would not be received in the event that said specimen were an ideally flat and smooth specimen.

13. The method according to claim 1, wherein said receiving is performed at a receiver that is configured for isolating sensitivity to spatial frequency content of the sample surface along predominantly one direction.

14. The method according to claim 1, wherein said receiving is performed at a receiver, and further comprising the step of receiving at a second receiver second optical radiation reflected or scattered from said specimen, said second optical radiation including specular components that are spatially encoded by wavelength according to chromatic aberration of the second receiver, and wherein said processing step includes processing a second signal representing said second optical radiation.

15. The method according to claim 14, wherein said receiver and second receiver are each respectively configured for isolating sensitivity to spatial frequency content of the sample surface along respective predominant directions of the sample.

16. The method according to claim 15, wherein said respective predominant directions are orthogonal to each other.

17. The method according to claim 14, wherein said optical signal and second optical signal are received concurrently.

18. The method according to claim 1, wherein said receiver provides the chromatic aberration.

19. The method according to claim 1, wherein said receiving is performed by at least one receiver that includes a specular component included (SCI) receiver.

20. An apparatus for characterizing surface effects of a specimen, comprising:
    means for receiving optical radiation from said specimen, said optical radiation including specular components that are spatially encoded by wavelength according to chromatic aberration; and
    a processor that provides a measure of surface characteristics of the specimen based on a signal representing said optical radiation which includes said specular components that are spatially encoded by wavelength according to chromatic aberration.

21. The apparatus according to claim 20, wherein said specimen is located at a sample port of an integrating sphere, and said means for receiving includes a specular-component excluded receiver disposed through a port of the integrating sphere.

22. The apparatus according to claim 20, further comprising a means for receiving a second optical signal from said specimen, said second optical signal including specular components reflected from said specimen.

23. The apparatus according to claim 22, wherein said optical signal and second optical signal are received concurrently.

24. The apparatus according to claim 20, wherein said processor processes said signal representing the optical radiation to provide a color measurement for said sample, thereby providing both color and surface effect characterization for said sample from a common measurement.

25. The apparatus according to claim 20, wherein said measure of surface characteristics is a surface effect index representative of surface roughness and is determined independently of calculating a function representing the spatial frequency content of the surface.

26. The apparatus according to claim 25, wherein said surface effect index is based on a deviation between specular reflectance for the measured specimen relative to an ideally flat and smooth specimen.

27. The apparatus according to claim 25, wherein said surface effect index is based on a shift in crossover frequency of specular error.

28. The apparatus according to claim 20, wherein said measure of surface characteristics is a function representing the spatial frequency content of the surface.

29. The apparatus according to claim 28, wherein said measure of surface characteristics is an appearance measure calculated according to said function representing the spatial frequency content of the surface.

30. The apparatus according to claim 29, wherein said appearance measure is an indication of gloss/matte, "orange peel", or gross flatness.

31. The apparatus according to claim 20, wherein said specular components would not be received in the event that said specimen were an ideally flat and smooth specimen.

32. The apparatus according to claim 20, wherein said means for receiving is configured for isolating sensitivity to spatial frequency content of the sample surface along predominantly one direction.

33. The apparatus according to claim 20, for comprising a means for receiving second optical radiation reflected or scattered from said specimen, said second optical radiation including specular components that are spatially encoded by wavelength according to chromatic aberration, and wherein said processor also processes a second signal representing said second optical radiation.

34. The apparatus according to claim 33, wherein said means for receiving optical radiation and means for receiving second optical radiation are each respectively configured for isolating sensitivity to spatial frequency content of the sample surface along respective predominant directions of the sample.

35. The apparatus according to claim 34, wherein said respective predominant directions are orthogonal to each other.

36. The apparatus according to claim 33, wherein said optical signal and second optical signal are received concurrently.

37. An apparatus for characterizing surface effects of a specimen, comprising:
a first receiver directed toward said specimen to receive first optical radiation reflected by said specimen, said first receiver having associated optics which provide chromatic aberration, said first optical radiation received by the first receiver including specular components that are spatially encoded by wavelength according to the chromatic aberration;
a beam shaper that, for a given said specimen, controls the relative amount of the specular components received by the first receiver as a function of direction along the specimen surface; and
a processor that processes a signal representing said optical radiation to generate a measure of surface characteristics of the specimen based on said specular components that are spatially encoded by wavelength according to chromatic aberration.

38. The apparatus according to claim 37, further comprising a second receiver that receives a second optical signal from said specimen, said second optical signal including total specular components reflected from said specimen.

39. The apparatus according to claim 38, wherein said optical signal and second optical signal are received concurrently.

40. The apparatus according to claim 37, wherein said processor processes said signal representing the optical radiation to provide a color measurement for said sample, thereby providing both color and surface effect characterization for said sample from a common measurement.

41. The apparatus according to claim 37, wherein said measure of surface characteristics is a surface effect index representative of surface roughness and is determined independently of calculating a function representing the spatial frequency content of the surface.

42. The apparatus according to claim 41, wherein said surface effect index is based on a deviation between specular reflectance for the measured specimen relative to an ideally flat and smooth specimen.

43. The apparatus according to claim 41, wherein said surface effect index is based on a shift in crossover frequency of specular error.

44. The apparatus according to claim 37, wherein said measure of surface characteristics is a function representing the spatial frequency content of the surface.

45. The apparatus according to claim 44, wherein said measure of surface characteristics is an appearance measure calculated according to said function representing the spatial frequency content of the surface.

46. The apparatus according to claim 45, wherein said appearance measure is an indication of gloss/matte, "orange peel", or gross flatness.

47. The apparatus according to claim 37, wherein said specular components would not be received in the event that said specimen were an ideally flat and smooth specimen.

48. The apparatus according to claim 37, further comprising:
a second receiver directed toward said specimen to receive second optical radiation reflected by said specimen, said second receiver having optics which provide chromatic aberration, said second optical radiation received by the second receiver including specular components that are spatially encoded by wavelength according to the chromatic aberration;
a second beam shaper that, for a given said specimen, controls the relative amount of the specular components received by the second receiver as a function of direction along the specimen surface; and
wherein said processor also processes a second signal representing said second optical radiation.

49. The method according to claim 48, wherein said first receiver and said beam shaper are configured to isolate sensitivity to spatial frequency content of the specimen surface along a predominant first direction of the specimen, and said second receiver and said second beam shaper are configured to isolate sensitivity to spatial frequency content of the sample surface along a predominant second direction of the specimen.

50. The method according to claim 47, wherein said first and second predominant directions are orthogonal to each other.

51. The method according to claim 48, wherein said optical signal and second optical signal are received concurrently.

52. The apparatus according to claim 37, further comprising an integrating sphere to which said first receiver is optically coupled for receiving said first optical radiation, and wherein said beam shaper is a port or trap of said integrating sphere, said port or trap disposed substantially opposite to said first receiver such that a specular projection of the first optical radiation received by the first receiver overlaps the region contained by the port or trap.

53. The apparatus according to claim 52, wherein said first receiver and said port or trap are configured to isolate sensitivity to spatial frequency content of the sample surface along predominantly one direction.

54. The apparatus according to claim 52, wherein along the periphery of said port or trap, said port or trap has a substantially equal amount of overlap with the specular projection relative to the specimen surface of the first optical radiation received by the first receiver, thereby providing a substantially equal amount of specular components received at the receiver as a function of direction along the specimen surface for a specimen having surface characteristics independent of direction along the specimen surface.

55. The apparatus according to claim 37, wherein said receiver includes a specular component included (SCI) receiver.

56. In an apparatus having a first receiver directed toward a specimen to receive optical radiation reflected by said specimen, and a beam shaper that, for a given said specimen, controls the relative amount of the specular components received by the first receiver as a function of direction along the specimen surface, a method for characterizing surface effects of the specimen, the method comprising the steps of:

adjusting the size of the beam shaper to each of a plurality of sizes;

receiving at the first receiver, for each of the plurality of sizes of said beam shaper, a corresponding optical radiation signal reflected or scattered from said specimen; and processing the corresponding optical radiation signals to provide a measure of surface characteristics.

57. The method according to claim 56, wherein said specimen is located at a sample port of an integrating sphere, and said receiver is a specular-component excluded receiver disposed through a port of the integrating sphere.

58. The method according to claim 56, further comprising the step of receiving a second optical signal from said specimen, said second optical signal including specular components reflected from said specimen.

59. The method according to claim 58, wherein said optical signal and second optical signal are received concurrently.

60. The method according to claim 56, wherein said processing step includes processing said signal representing optical radiation to provide a color measurement for said sample, thereby providing both color and surface effect characterization for said sample from a common measurement.

61. The method according to claim 56, wherein said measure of surface characteristics is a surface effect index representative of surface roughness and is determined independently of calculating a function representing the spatial frequency content of the surface.

62. The method according to claim 61, wherein said surface effect index is based on a deviation between specular reflectance for the measured specimen relative to an ideally flat and smooth specimen.

63. The method according to claim 61, wherein said surface effect index is based on a shift in crossover frequency of specular error.

64. The method according to claim 56, wherein said measure of surface characteristics is a function representing the spatial frequency content of the surface.

65. The method according to claim 64, wherein said measure of surface characteristics is an appearance measure calculated according to said function representing the spatial frequency content of the surface.

66. The method according to claim 65, wherein said appearance measure is an indication of gloss/matte, "orange peel", or gross flatness.

67. The method according to claim 56, wherein said receiver is configured for isolating sensitivity to spatial frequency content of the sample surface along predominantly one direction.

68. The method according to claim 56, wherein the apparatus includes a second receiver directed toward the specimen to receive second optical radiation reflected by said specimen, and a second beam shaper that, for a given said specimen, controls the relative amount of the specular components received by the second receiver as a function of direction along the specimen surface, the method further comprising the steps of:

adjusting the size of the second beam shaper to each of a plurality of sizes;

receiving at the second receiver, for each of the plurality of sizes of said second beam shaper, a corresponding second optical radiation signal reflected or scattered from said specimen; and processing the corresponding second optical radiation signals to provide a measure of surface characteristics.

69. The method according to claim 68, wherein said first receiver and second receiver are each respectively configured for isolating sensitivity to spatial frequency content of the sample surface along respective predominant directions of the sample.

70. The method according to claim 69, wherein said respective predominant directions are orthogonal to each other.

71. The method according to claim 68, wherein said first optical radiation signal and second optical radiation signal are received concurrently.

72. The apparatus according to claim 51, further comprising an integrating sphere to which said first receiver is optically coupled for receiving said first optical radiation, and wherein said beam shaper is a port or trap of said integrating sphere, said port or trap disposed substantially opposite to said first receiver such that a specular projection of the first optical radiation received by the first receiver overlaps the region contained by the port or trap.

* * * * *